(12) United States Patent
Sasaki et al.

(10) Patent No.: US 9,753,048 B2
(45) Date of Patent: Sep. 5, 2017

(54) SAMPLE TEST AUTOMATION SYSTEM

(75) Inventors: Takahiro Sasaki, Hitachinaka (JP); Kenichi Takahashi, Naka (JP); Hiroshi Ohga, Hitachiomiya (JP); Tatsuya Fukugaki, Hitachinaka (JP); Shigeru Yano, Hitachinaka (JP); Kenichi Yasuzawa, Hitachinaka (JP); Nozomi Hasegawa, Hitachinaka (JP); Masaaki Hanawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 757 days.

(21) Appl. No.: 13/699,646

(22) PCT Filed: May 23, 2011

(86) PCT No.: PCT/JP2011/061759
§ 371 (c)(1),
(2), (4) Date: Nov. 23, 2012

(87) PCT Pub. No.: WO2011/148897
PCT Pub. Date: Dec. 1, 2011

(65) Prior Publication Data
US 2013/0061693 A1    Mar. 14, 2013

(30) Foreign Application Priority Data

May 24, 2010  (JP) ................. 2010-118028
Jul. 14, 2010  (JP) ................. 2010-159260
Jul. 20, 2010  (JP) ................. 2010-162407

(51) Int. Cl.
*G01N 1/22*       (2006.01)
*G01N 35/02*      (2006.01)
*G01N 35/00*      (2006.01)

(52) U.S. Cl.
CPC ..... *G01N 35/026* (2013.01); *G01N 35/00732* (2013.01); *G01N 2035/00801* (2013.01)

(58) Field of Classification Search
CPC ......... G01N 35/00732; G01N 35/0099; G01N 35/026
(Continued)

(56) References Cited

U.S. PATENT DOCUMENTS 3,526,125 A * 9/1970 Emary ................. B01L 3/5453
                                                              101/35
6,255,614 B1    7/2001 Yamakawa et al.
(Continued)

FOREIGN PATENT DOCUMENTS

JP    07-167866 A    7/1995
JP    11-83865 A     3/1999
(Continued)

OTHER PUBLICATIONS

International Preliminary Report on Patentability for PCT/JP2011/061759, report isuued Dec. 10, 2012.*
(Continued)

*Primary Examiner* — Lisa Caputo
*Assistant Examiner* — Rodney T Frank
(74) *Attorney, Agent, or Firm* — Mattingly & Malur, PC

(57) ABSTRACT

A sample test automation system which is capable of reducing the workload of an operator and precisely carrying out necessary processes of each of samples without stagnation. In the sample test automation system, a sample tray 120 on which a plurality of samples 150 can be installed is prepared, an identifier for distinguishing the sample tray 120 is attached to the sample tray 120, a sample introducing unit 10 is provided with an identifier reading apparatus 111 which
(Continued)

reads the identifier of the sample tray 120, and information about the samples 150 is switched based on the read identifier of the sample tray 120.

5 Claims, 32 Drawing Sheets

(58) Field of Classification Search
USPC .................................................. 73/863.01
See application file for complete search history.

(56) References Cited

U.S. PATENT DOCUMENTS

| | | | |
|---|---|---|---|
| 8,859,289 B2 | 10/2014 | Marty et al. | |
| 2005/0186114 A1* | 8/2005 | Reinhardt | B01L 9/52 422/65 |
| 2007/0172396 A1* | 7/2007 | Neeper | G01N 35/00732 422/400 |
| 2010/0126286 A1* | 5/2010 | Self | G01N 35/04 73/863.81 |

FOREIGN PATENT DOCUMENTS

| | | |
|---|---|---|
| JP | 11-083866 A | 3/1999 |
| JP | 11-304812 A | 11/1999 |
| JP | 2000321287 | 11/2000 |
| JP | 2001-004639 A | 1/2001 |
| JP | 2001-021569 A | 1/2001 |
| JP | 2001-124783 A | 5/2001 |
| JP | 2002-120913 A | 4/2002 |
| JP | 2002-181835 A | 6/2002 |
| JP | 2004093518 | 3/2004 |
| JP | 2006030035 | 2/2006 |
| JP | 2007309675 | 11/2007 |
| JP | 2008-122205 A | 5/2008 |
| JP | 2009-036643 A | 2/2009 |
| JP | 2009-222535 A | 10/2009 |
| JP | 2010-014441 A | 1/2010 |
| JP | 2010032517 | 2/2010 |
| JP | 2010107464 | 5/2010 |
| WO | 2009002358 | 12/2008 |

OTHER PUBLICATIONS

Japanese Office Action dated Apr. 28, 2015, issued in corresponding Japanese Patent Application No. 2014-077312.

* cited by examiner

| | BLOOD SERUM | BLOOD PLASMA | URINE | |
|---|---|---|---|---|
| ROUTINE | 1-20 | 21-30 | 31-35 | |
| SEPARATED BY CENTRIFUGATION | 41-44 | 45-47 | 48-49 | |
| NO CAP | 51-54 | 55-57 | 58-59 | |
| STAT | 91-94 | 95-97 | 98-99 | |

FIG. 7

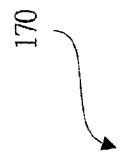

- 171 — 0 ··· TYPE OF SAMPLE (0: BLOOD SERUM, 1: BLOOD PLASMA, 2: URINE, 3: BLOOD CELL)
- 172 — 1 ··· CENTRIFUGAL PROCESS (0: UNNECESSARY, 1: NECESSARY)
- 173 — 1 ··· DECAPPING PROCESS (0: UNNECESSARY, 1: NECESSARY)
- 174 — 0 ··· RECAPPING PROCESS (0: UNNECESSARY, 1: NECESSARY)
- 175 — 2 ··· CONVEYANCE DESTINATION (0: AUTOMATIC ANALYZING APPARATUS, 1: SORTING UNIT, 2: STORAGE UNIT)
- 176 — 1 ··· PRIORITY (0: ROUTINE, 1: STAT)
- 177 — 3 ··· CONTAINER SHAPE (0: TYPE A, 1: TYPE B, 2: TYPE C, 3: TYPE D)

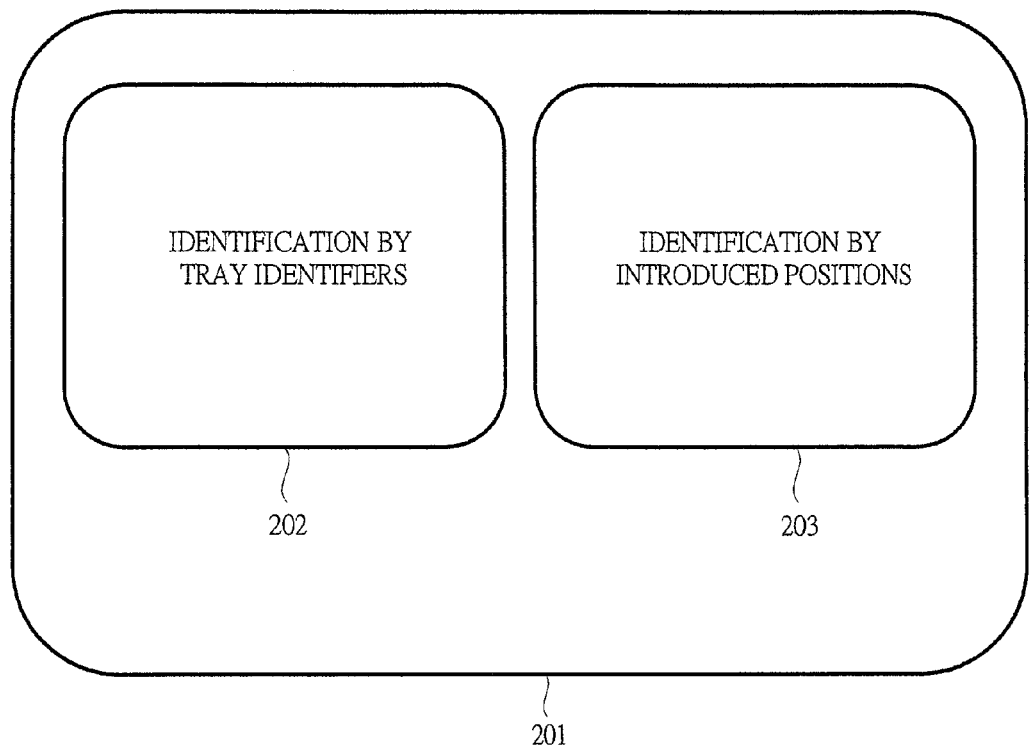

FIG. 24

STORAGE UNIT TRAY SETTING PARAMETERS

TRAY INFORMATION — 320

| DIVIDED TRAY | SENSOR POSITION | TRAY LENGTH/WIDTH | TRAY ID |
|---|---|---|---|
| TRAY 1 | 1 | 5×10 | 00001~99950 |
| TRAY 2 | 2 | 5×10 | 00001~99950 |
| TRAY 3 | 3 | 5×10 | 00001~99950 |
| TRAY 4 | 4 | 5×10 | 00001~99950 |
| TRAY 5 | 5 | 5×10 | 00001~99950 |
| TRAY 6 | 6 | 5×10 | 00001~99950 |
| TRAY 7 | 7 | 5×10 | 00001~99950 |
| TRAY 8 | 8 | 3×10 | 99951~99999 |
| TRAY 9 | 8 | 2×10 | 99951~99999 |

| TRAY INFORMATION INITIALIZATION |
|---|

TRAY ID
05001
05002
05003
05004
05005
05006
05007
05008
05009
05010

| TRAY EXPIRE DATE PARAMETERS |
|---|

TRAY EXPIRE DATE

| TRAY ID RANGE | EXPIRE DATE |
|---|---|
| 00001~99900 | 7 |
| 99901~99950 | 3 |
| 99951~99999 | 1 |

FIG. 29

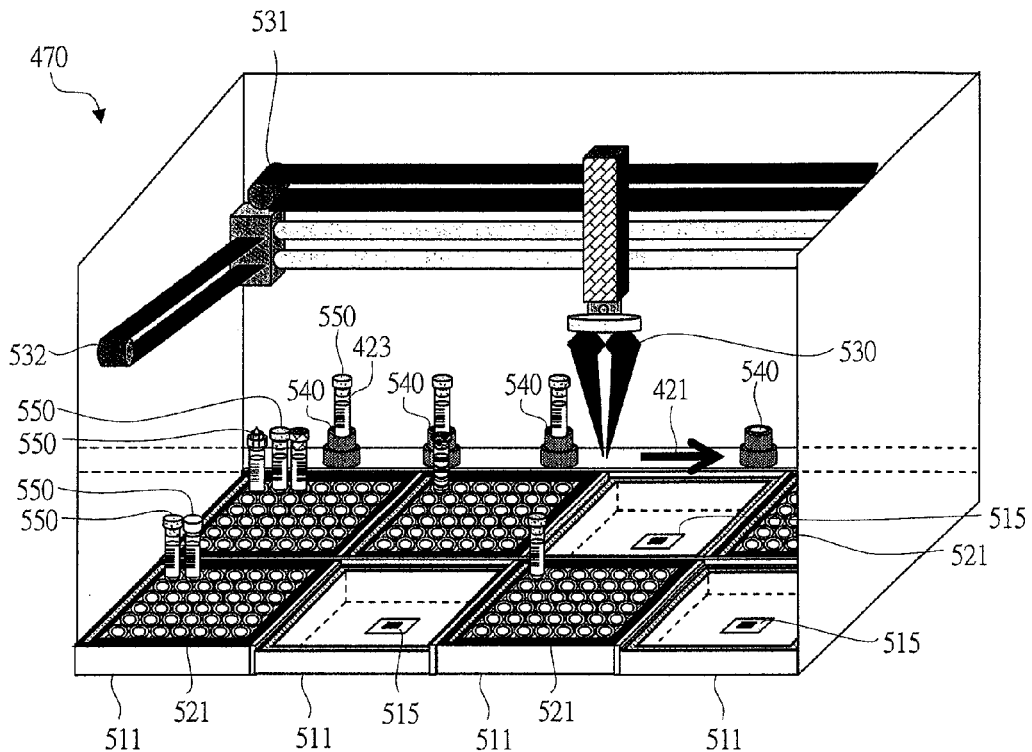

FIG. 30

|  | ERROR-SAMPLE TYPE INFORMATION | MODULE INFORMATION | SAMPLE TRAY INSTALLATION UNIT INFORMATION | INFORMATION OF POSITIONS IN SAMPLE TRAY |
|---|---|---|---|---|
| 210 | SAMPLE IDENTIFIER UNREADABLE | SAMPLE INTRODUCING UNIT | Ch4 | 1~20 |
| 220 | SAMPLE INFORMATION UNOBTAINABLE | SAMPLE INTRODUCING UNIT | Ch4 | 21~40 |
| 230 | CENTRIFUGAL SEPARATION PROCESS INTERRUPTION | SAMPLE STORAGE UNIT | Ch8 | All (1 to 50) |
| 240 | DECAPPING PROCESS FAILURE | SAMPLE INTRODUCING UNIT | Ch4 | 41~50 |
| 250 | ALIQUOTING FAILURE | SAMPLE INTRODUCING UNIT | Ch3 | All (1~50) |

SAMPLE TEST AUTOMATION SYSTEM

TECHNICAL FIELD

The present invention relates to a sample test automation system that processes samples of blood, urine, etc. in clinical tests and particularly relates to sorting of the samples upon sample introduction.

The present invention also relates to a sample test automation system provided with a function of reducing recovery process operations in a case in which errors have occurred in the system.

BACKGROUND ART

The sample test automation system is a system which automates processes such as centrifugal separation, decapping, aliquot sample aliquoting, barcode attaching, and aliquot sample sorting. The samples handled by the sample test automation system are biological samples such as blood (whole blood, blood serum, blood plasma) and urine. The state of the samples upon introduction into the sample test automation system is various, and processing contents are therefore different for each sample.

Examples of actual management include: a situation in which the samples which have undergone and not have undergone centrifugal separation are mixed, a case in which so-called Short Turn Around Time (STAT) samples which require prioritized processing are suddenly inserted, and a case in which processing contents are different depending on the types of the sample containers. The processes having different contents have to be carried out for each of the samples in accordance with the management, respectively.

With respect to these needs, conventionally, a conveying method using a sample rack on which a plurality of samples can be installed has been employed to manage information imparting to the rack. Through a method of imparting information such as the types of samples (identification of sample types, distinguishment of routine/calibrator/precision control) and processing contents to the range of the number of an identifier attached to the rack or the color or shape of the rack, samples are automatically sorted to handle above-described various situations.

For example, in Japanese Patent Application Laid-Open Publication No. H11-083866 (Patent Document 1), a dedicated number is imparted to a rack on which STAT samples are placed, and the samples are conveyed to necessary conveyance destinations based on the conveyance information read from the rack. Japanese Patent Application Laid-Open Publication No. H11-304812 (Patent Document 2) describes a method of a measure against a case in which a reading error of the identifier of the rack occurs.

Containers storing samples such as blood or urine are loaded on a rack or a container for conveying samples called a sample container holder or the like and are supplied to the sample test automation system. Depending on the test items to be measured and the contents of preprocessing, the samples are subjected to, for example, a centrifugal separation process, a decapping process of decapping caps of the containers, a process of aliquoting the sample to one or more different containers, i.e., an aliquoting process from a primary sample to aliquot sample containers in accordance with use; a process of attaching barcode labels on aliquot sample containers, a recapping process of closing the aliquot sample containers with the caps, a sorting storage process of sorting primary samples and aliquot samples in accordance with the processes thereafter, and a process of conveying an aliquot sample rack to an automatic analyzing apparatus and analyzing and measuring aliquot samples. Apparatuses having functions of these processes are connected by a plurality of conveyance lines to constitute a sample test automation system.

Such a sample test automation system is described in, for example, Japanese Patent Application Laid-Open Publication No. H7-167866 (Patent Document 3).

In addition, the sample test automation system contributes to shifting test room operators to operations of higher value by significantly automating repeated operations in a test room. In operation of this system, some parts have not been completely automated yet. Typical ones include supply of consumable items, carry-in/out of samples, and recovery processes upon error occurrence.

If an error occurs in the course of a process with respect to the samples, the error-occurred samples have to be separated from normal samples and taken out to outside the system. In Japanese Patent Application Laid-Open Publication No. 2009-222535 (Patent Document 4), working efficiency is improved by customizing sample carrying-out destinations on an automatic analyzing apparatus in accordance with management. In Japanese Patent Application Laid-Open Publication No. 2009-36643 (Patent Document 5), carrying-out patterns are controlled respectively for types of samples, for example, respectively for patients or hospital wards upon carry-out of the samples to sample trays to improve ease in handling of the samples.

PRIOR ART DOCUMENTS

Patent Documents

Patent Document 1: Japanese Patent Application Laid-Open Publication No. H11-083866
Patent Document 2: Japanese Patent Application Laid-Open Publication No. H11-304812
Patent Document 3: Japanese Patent Application Laid-Open Publication No. H7-167866
Patent Document 4: Japanese Patent Application Laid-Open Publication No. 2009-222535
Patent Document 5: Japanese Patent Application Laid-Open Publication No. 2009-36643

DISCLOSURE OF THE INVENTION

Problems to be Solved by the Invention

Meanwhile, today, not only a conveyance system using the sample rack, but also a conveyance system using a sample holder on which only one sample is installed is also common. This conveyance system has advantages for individual processing of samples, for example, the samples are not required to be collected in a rack, and delay of processes and accompanying conveyance due to waiting for filling of the rack can be avoided.

However, this conveyance system in this state is not suitable for mass processing. Therefore, in order to prevent reduction in processing ability, a sample tray on which a plurality of samples can be installed has been conventionally employed in a sample introducing unit as means for substituting for the rack. Different uses of sample trays such as those carried out in the conventional conveyance systems using racks as described in Patent Documents 1 and 2 are not employed. Therefore, for individual samples, the samples and the information about the samples such as processing methods have to be input in detail through a screen of an operation unit, and the load of operators is large.

In this manner, conventionally, there has been a problem that the operation of inputting related information has been required for every sample upon introduction of samples in the system that carries out conveyance by the sample holder on which only one sample is installed.

Moreover, a primary sample of which preprocessing has been finished is normally sorted in a sorting process and set to a predetermined tray; or, if the container for conveying the primary sample is, for example, a rack, the primary sample is stored in a state that it is installed in the rack.

If an add-on test or addition of test items is ordered from a test room information system (Laboratory Information System, hereinafter, abbreviated as LIS), which is a higher-order system of the sample test automation system, the current position of the primary sample is searched by using a monitor of an operation unit provided in the sample test automation system, and, by manual operation, the primary sample is taken out from the tray or the rack on which the primary sample is installed is taken out from the searched and found out location and is introduced again to an introducing unit to carry out management. However, many sample containers and sample racks are arranged in the storing location of the primary sample, and the operation of taking out the objective primary sample or the rack on which the primary sample is installed by manual operation is not only cumbersome and non-efficient, but can also induce human errors such as mix-up of samples. Also, the risk of infection caused by direct contact with the samples is conceivable.

Furthermore, since the carrying-out destinations of error samples have been fixed in conventional systems, the carrying-out location of the error samples and the carrying-in locations after recovery processes are distant from each other depending on the system layout, the moving distance of operators is long, and working efficiency has been reduced in some cases.

When a recovery process operation of a sample for which some sort of error has occurred is to be carried out in the sample test automation system, in the current sample test automation system, the operator has to see a screen or a record file in order to find out what kind of recovery process should be carried out.

In a case in which an error sample is generated, if an alarm is generated immediately after the error has occurred in the device configuration in which various processing units and a carrying-out location of the error sample are distant from each other, the operator arrives at the carrying-out location before the error sample arrives at the carrying-out destination, and the operator has to wait in some cases.

In view of the above-described problems, it is a preferred aim of the present invention to provide a sample test automation system capable of proposing a uniformed sample recognizing method, reducing the workload of operators, and precisely carrying out processes respectively required for samples without stagnation.

It is another preferred aim of the present invention to provide a sample test automation system that realizes simple operation while preventing mix-up of samples by manual operation of test technicians who are system users and avoiding the risk of infection.

The above and other preferred aims and novel characteristics of the present invention will be apparent from the description of the present specification and the accompanying drawings.

Means for Solving the Problems

A summary of the inventions disclosed in the present application will be briefly described as follows.

Specifically, a sample tray on which a plurality of samples can be installed is prepared; an identifier for distinguishing the sample tray is attached to the sample tray, a sample introducing unit has an identifier reading apparatus that reads the identifier attached to the sample tray; and an operation control unit switches and controls information about the samples installed on the sample tray based on the identifier attached to the sample tray, the identifier having been read by the identifier reading apparatus. An outline of the present invention for achieving above-described another object will be explained as below.

More specifically, sample test automation system includes: an introducing unit that introduces samples; a processing unit that preprocesses the samples; a storage unit that stores preprocessing-finished samples; a sample conveyance line that conveys the samples between the introducing unit; the processing unit, and the storage unit; and an operation unit that controls the introducing unit, the processing unit, and the storage unit; using trays that can be shared by the introducing unit and the storage unit. The tray is provided with an identifier storing identification information about the tray per se and the samples installed on the tray. An apparatus that reads/writes the identification information from/to the identifier by means such as wireless communication is installed at the introducing unit and the storage unit. A mechanism that writes the latest identification information about the sample installed on the tray and at least the usage state of the tray to the identifier when an operation of taking out the tray is carried out in the storage unit is provided. A mechanism that reads the identification information about the sample installed on the tray and at least the usage state of the tray from the identifier when an operation of introducing the tray is carried out in the introducing unit is provided. An operation unit that has means for communicating with the introducing unit and the storage unit and has a control process of sending various orders to the introducing unit and the storage unit as a result of sending/receiving of the identification information by the communication means is provided. The operation unit is provided with a function of notifying a test technician of the fact that the sample for which an add-on test or addition of a test item is to be carried out is installed on the tray taken out from the storage unit; and the operation unit is provided with a function of notifying the test technician of the fact that the sample to be re-transferred (re-reformatted) is not installed on the tray introduced to the introducing unit. Other outlines of the invention disclosed in the present application will be explained as follows.

A mechanism capable of arbitrarily setting the carrying-out destination of an error sample in accordance with layout or management is provided. As a result, a layout or workflow taking, for example, the moving distance to the position of a working desk in a test room or to a re-carry-in location after finishing a recovery process by manual operation into consideration can be achieved.

Moreover, a mechanism that distinguishes a conveyance destination for each of the types and recovery processing methods of error samples is provided. As a result, the type or recovery method of the error can be found out from the conveyance destination; therefore, the operator is not required to see a screen or a record file upon a recovery process.

Moreover, means for changing the timing of an error notification to the timing when the error sample is carried out instead of the timing of generation of the error sample is provided.

In accordance with the management mode of the test room which is a facility utilizing the system, the processing unit is provided with a group of required apparatuses, and the sample test automation system capable of handling various processes can be built. In the present specification, descriptions about components of the processing unit will be omitted; however, every processing apparatus does not impair the range of implementation influence of the present invention.

Effects of the Invention

The effects obtained by typical aspects of the present invention will be briefly described below.

An effect obtained by typical aspects is that each sample can be individually subjected to a process having different contents by switching the sample information based on the identifier attached to the sample tray on which samples are installed. When the operator once registers the information linked to the information about the identifier attached to the sample tray and about the sample, the operation of inputting processing contents every time for each sample becomes unnecessary in the management thereafter. Since the function by which the operator can arbitrarily set a management method is provided, management adapted for the individual environment of a test room can be carried out.

Effects obtained by another invention disclosed in the present application will be described below.

In the sample test automation system, simple operability can be realized while preventing mix-up of samples by manual operation and avoiding the risk of infection.

Moreover, according to the present invention, the conveyance destination can be also customized depending on the layout or management of each test room; therefore, the moving route of operators can be optimized to improve working efficiency.

Moreover, since the carrying-out destinations of the error samples are sorted for each type or recovery processing method, the operator can immediately start a recovery operation at the point when he/she touches the error sample without seeing a screen or a record file.

Furthermore, when the operator arrives at the carrying-out destination of the error samples, the error samples have already arrived always; therefore, wasteful waiting time is not generated.

According to combinations of the foregoing, the recovery operation for the error samples in the sample test automation system according to the present invention can be more smoothly carried out. Furthermore, the effect of reduction in operation errors can be also expected since the referencing operation is eliminated.

BRIEF DESCRIPTIONS OF THE DRAWINGS

FIG. 7 is an explanatory diagram for explaining a method of attaching the identifiers to the trays of the sample test automation system according to the embodiment of the present invention;

FIG. 10 is a diagram illustrating an example of a first layer screen of a setting screen of a sample test automation system according to the embodiment of the present invention;

FIG. 11 is a diagram illustrating an example of a second layer screen of the setting screen of the sample test automation system according to the embodiment of the present invention;

FIG. 24 is a diagram illustrating a screen example of storage unit tray setting parameters displayed by an operation unit;

FIG. 25 is a diagram illustrating an example of a tray information initializing screen displayed by the operation unit;

FIG. 26 is a diagram illustrating an example of a tray expire date parameter screen displayed by the operation unit;

FIG. 29 is a configuration diagram of a sorting unit;

FIG. 30 shows a setting example of types of error samples and conveyance destinations;

BEST MODE FOR CARRYING OUT THE INVENTION

Hereinafter, embodiments of the present invention will be described in detail with reference to the accompanying drawings. Note that components having the same function are denoted by the same reference symbols in principle throughout the drawings for describing the embodiment, and the repetitive description thereof will be omitted.

<1. System Outline>

Figure 1:
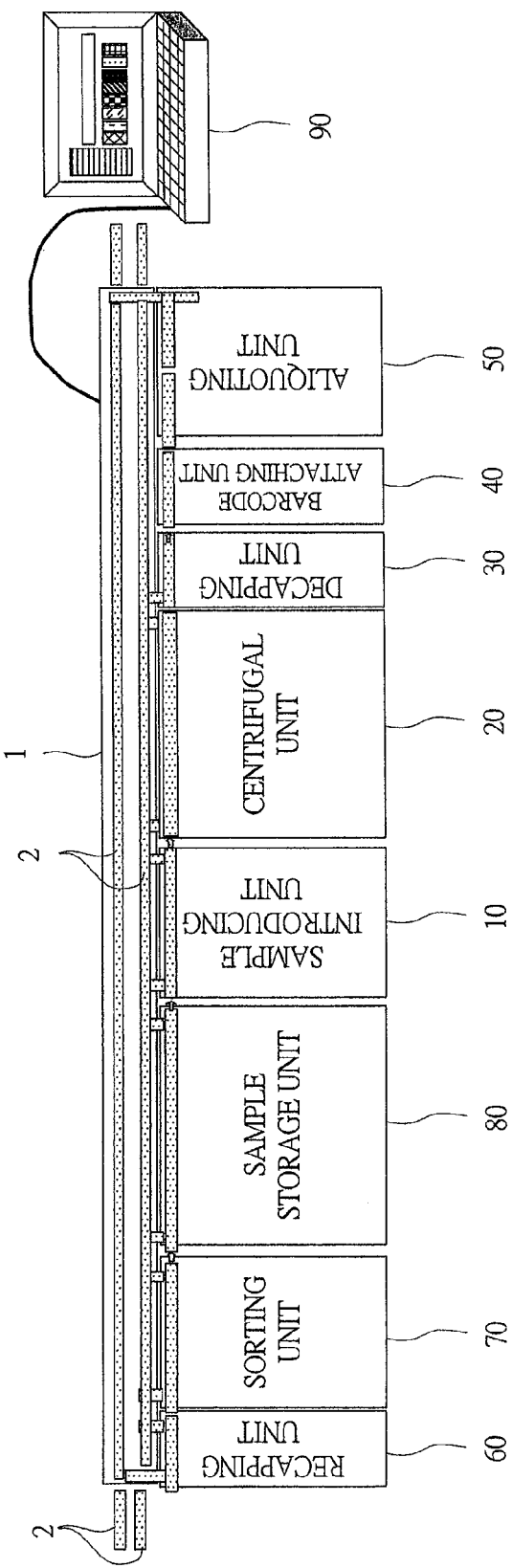
FIG. 1 is a configuration diagram illustrating an overall configuration of a sample test automation system according to an embodiment of the present invention.
Figure 2:
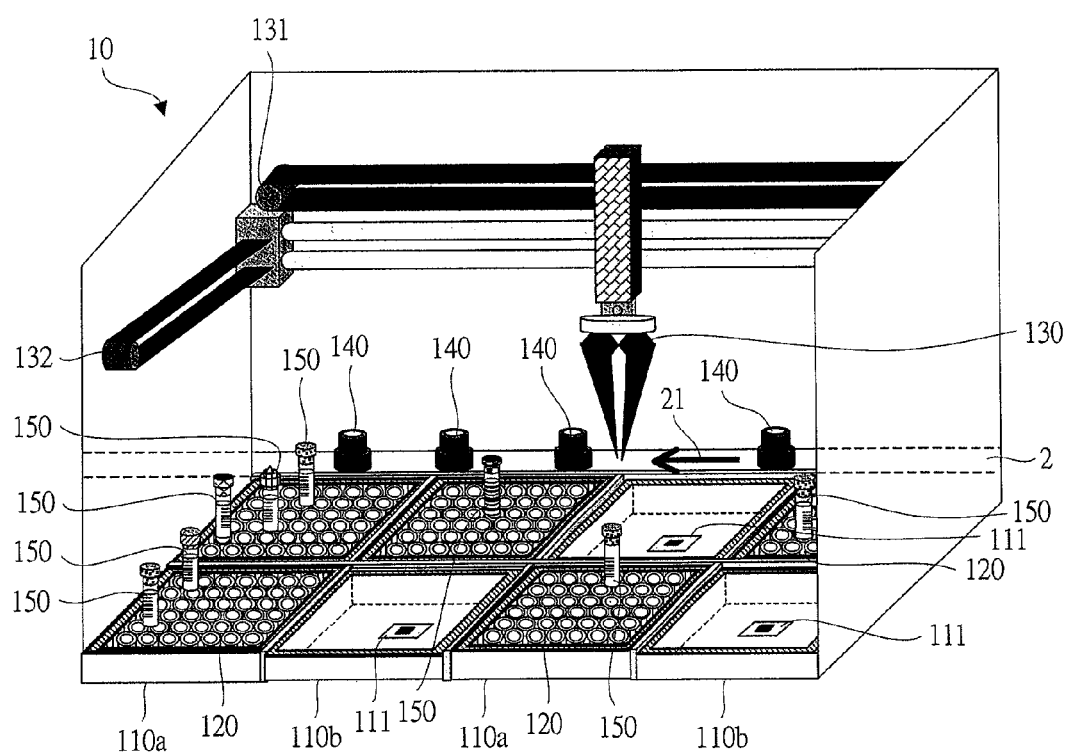
FIG. 2 is a configuration diagram illustrating a configuration of a sample introducing unit of the sample test automation system according to the embodiment of the present invention.
Figure 3:
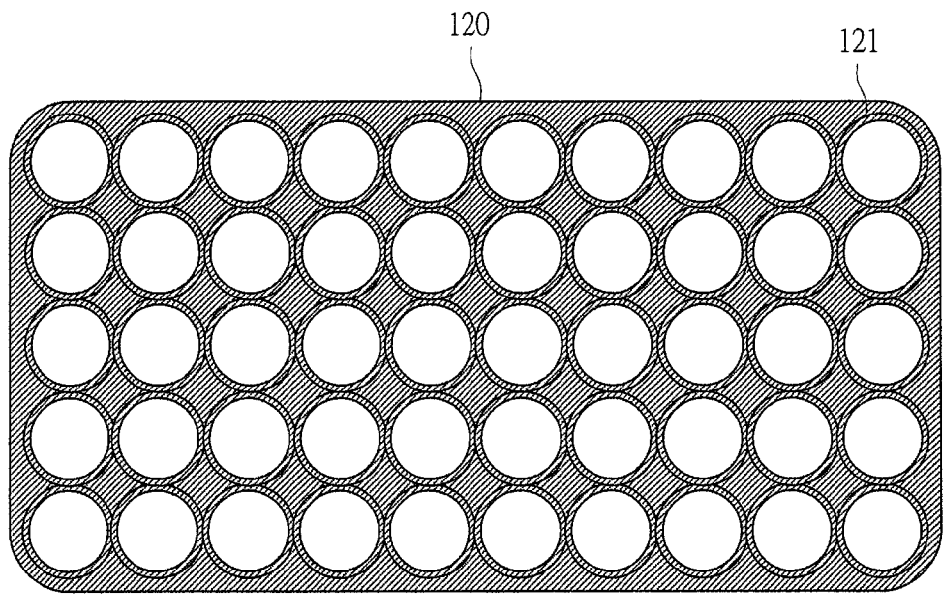
FIG. 3 is a diagram illustrating an example of a sample tray of the sample test automation system according to the embodiment of the present invention.
Figure 4:
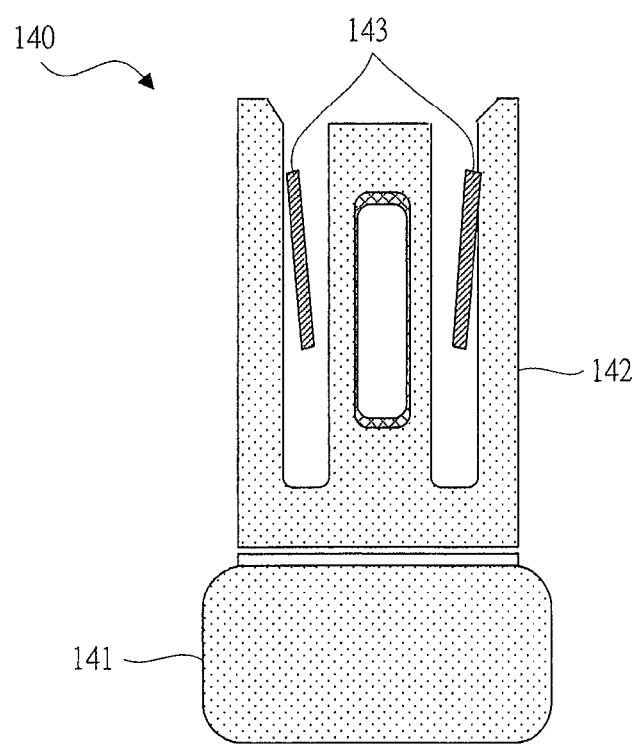
FIG. 4 is a diagram illustrating an example of a sample holder of the sample test automation system according to the embodiment of the present invention.
Figures 5, 6:
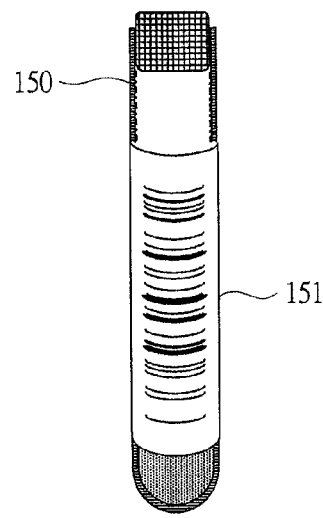
FIG. 5 is a diagram illustrating an example of a sample of the sample test automation system according to the embodiment of the present invention.
FIG. 6 is an explanatory diagram for explaining a method of attaching identifiers to trays of the sample test automation system according to the embodiment of the present invention.

According to FIGS. 1 to 5, a configuration of a sample test automation system according to an embodiment of the present invention will be described. FIG. 1 is a configuration diagram illustrating an overall configuration of the sample test automation system according to the embodiment of the present invention, FIG. 2 is a configuration diagram illustrating a configuration of a sample introducing unit of the sample test automation system according to the embodiment of the present invention, FIG. 3 is a diagram illustrating an example of a sample tray of the sample test automation system according to the embodiment of the present invention, FIG. 4 is a diagram illustrating an example of a sample holder of the sample test automation system according to the embodiment of the present invention, and FIG. 5 is a diagram illustrating an example of a sample of the sample test automation system according to the embodiment of the present invention.

In FIG. 1, the sample test automation system 1 is composed of the sample introducing unit 10, a centrifugal unit 20, a decapping unit 30, a barcode attaching unit 40, an aliquoting unit 50, a recapping unit 60, a sorting unit 70, a sample storage unit 80, a conveying unit 2, and an operation control unit (operating personal computer) 90, which carries out operation and control of the whole sample test automation system 1. The configuration illustrated in FIG. 1 is an example and is not intended to limit them to the layout illustrated herein.

In the sample introducing unit 10, samples are introduced into the sample test automation system 1; and, in the centrifugal unit 20, the introduced samples are subjected to centrifugal separation. In the decapping unit 30, caps of the samples, which have undergone centrifugal separation, are opened; and, in the aliquoting unit 50, the samples, which have undergone centrifugal separation, are separated into small portions in order to subject them to analysis by, for example, external analyzing apparatuses. In the barcode attaching unit 40, barcodes are attached onto containers of the small portions.

In the recapping unit 60, the samples are closed with the caps; and, in the sample storage unit 80, the samples closed with the caps are stored. In the sorting unit 70, aliquoted sample containers are sorted.

In FIG. 2, the sample introducing unit 10 is mainly composed of elements, i.e., the conveying unit 2, tray storage units 110 (110a, 110b), sample trays 120, an arm 130, and sample holders 140. Samples (test tubes/blood collection tubes) 150 are installed on the sample trays 120.

In FIG. 2, the tray storage units 110 denoted with 110a show a state in which the sample tray 120 is stored in the tray storage unit 110 and the tray storage units 110 denoted with 110b show a state in which no sample tray 120 is housed in the tray storage unit 110.

As illustrated in FIG. 3, the sample tray 120 is provided with a plurality of sample storage holes 121. Further, as illustrated in FIG. 4, the sample holder 140 is composed of a base 141, an outer wall 142, and supports 143. Furthermore, as illustrated in FIG. 5, an identifier such as a barcode 151 is attached on the sample 150.

The conveying unit 2 conveys the sample holder 140 illustrated in FIG. 4 along a path. In the present embodiment, the sample holders are conveyed in the direction of an arrow 21 in FIG. 2. The sample tray 120 is housed in the tray storage unit 110 (110a, 110b). A sensor (identifier reading apparatus) 111 is installed at a bottom part of the tray storage unit 110 (110a, 110b).

Although not illustrated in FIG. 2, an identifier is attached to the bottom of the sample tray 120, and a mechanism that reads the identifier by the sensor (identifier reading apparatus) 111 at the same time as installation is implemented.

For example, a one-dimensional barcode, two-dimensional barcode, or RFID is adopted as the identifier.

As illustrated in FIG. 3, the plurality of sample storage holes 121 are provided on the sample tray 120, and the samples 150 corresponding to the maximum number of the holes can be installed therein. Belts are installed at the arm 130, and the arm can be moved lengthwise, widthwise, and vertically via motors (131, 132).

An operator installs the samples 150, to which the identifiers are attached, on the sample tray 120 and sets that in the sample introducing unit 10. This setting serves as a signal to start an automation process by the apparatus. The sample introducing unit 10 picks up the samples 150 on the sample tray 120 by the arm 130 and installs the samples in the sample holders 140 prepared on the conveying unit 2.

The base 141 in a circular shape as illustrated in FIG. 4 is attached to the sample holder 140, and the sample holder can be therefore moved on the conveying unit 2 without deviating therefrom. The diameter of the outer wall 142 has a fixed value, and the supports 143 are attached thereto so that the sample 150 having a different diameter can be installed therein.

Then, the samples 150 are placed on the sample holders 140 and sequentially go through, for example, the centrifugal unit 20, the decapping unit 30, the barcode attaching unit 40, the aliquoting unit 50, the recapping unit 60, the sorting unit 70, and the sample storage unit 80 to undergo processes in the respective parts.

When the samples 150 are to be picked up in the sample introducing unit 10, the sample storage holes 121 are sequentially probed in each sample tray 120 from the left back to the right front thereof; and, if no sample 150 is detected consecutively in a predetermined number or more of the sample storage holes 121, it is considered that this sample tray 120 has no sample 150, and probing of the next tray 120 is carried out. Alternatively, a method of installing a camera from the upper surface of the sample introducing unit 10 and installing a function that automatically recognizes the sample storage holes 121 with the samples 150 is also effective.

<2. Switching of Information about Samples and Management Method>

Figure 8:
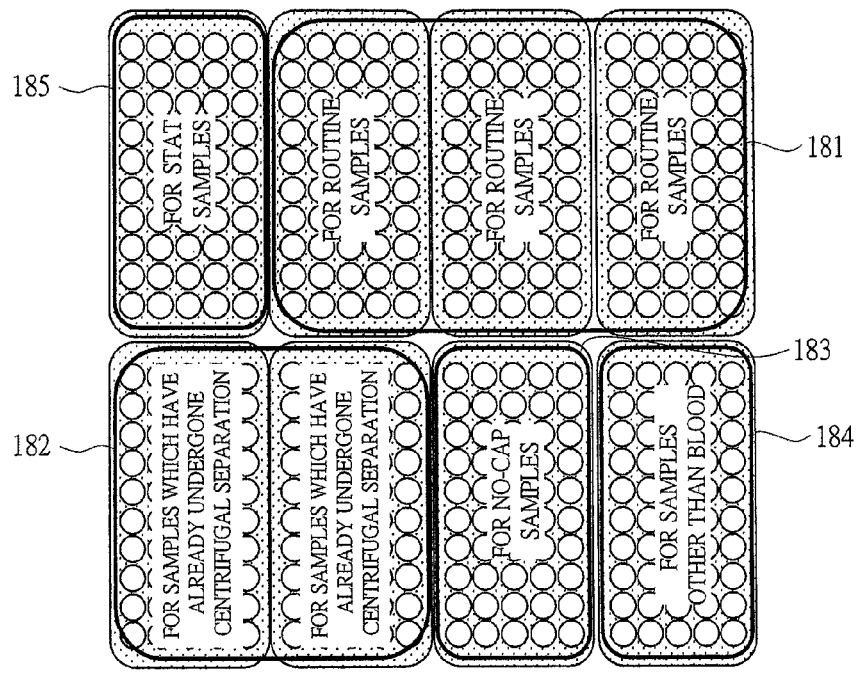
FIG. 8 is an explanatory diagram for explaining a method of imparting information to locations of the sample test automation system according to the embodiment of the present invention.
Figure 9:
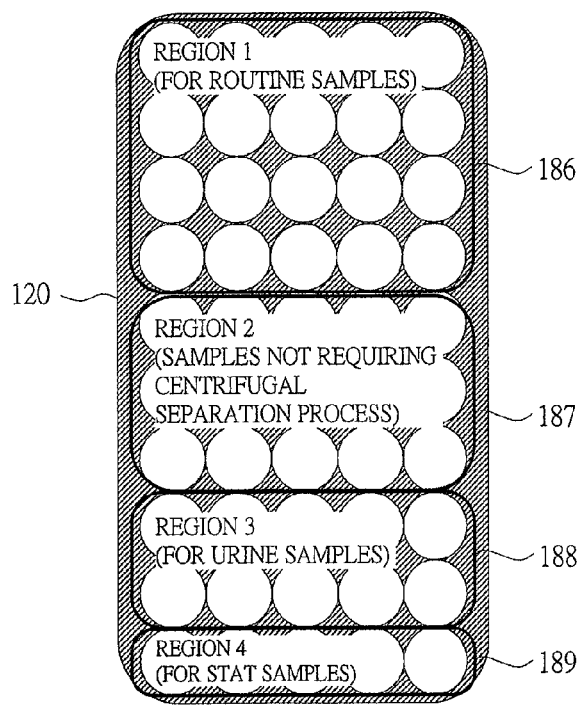
FIG. 9 is an explanatory diagram for explaining a method of logically compartmentalizing the trays of the sample test automation system according to the embodiment of the present invention.

Next, switching of information about the samples of the sample test automation system according to the embodiment of the present invention and a management method will be described with reference to FIGS. 6 to 9. FIGS. 6 and 7 are explanatory diagrams for explaining a method of attaching the identifiers to the trays of the sample test automation system according to the embodiment of the present invention, FIG. 8 is an explanatory diagram for explaining a method of imparting information to locations of the sample test automation system according to the embodiment of the present invention, and FIG. 9 is an explanatory diagram for explaining a method of logically compartmentalizing the trays of the sample automation system according to the embodiment of the present invention.

The course of processes of the samples is determined according to information such as the types of the samples, the degrees of urgency, etc. The samples include not only patient samples but also calibrators and precision control samples as samples for controlling the system, and it is important to identify them and cause the system to recognize them.

In the present embodiment, the above-described types of the samples are identified, and the sample test automation system is caused to recognize the information about the samples such as processing contents by a following method.

First, under the premise on all the above-described operations, an operator links the identifiers and the information about the samples to each other in advance and inputs the information from the operation control unit 90 to register the information. The contents of the operations are only required to be input once upon purchase or upon maintenance of the sample test automation system and are saved even when the power supply of the sample test automation system is turned off. Once the information is registered, constant management in accordance with setting is carried out unless the information is changed thereafter.

(1) Method of Attaching Identifier to the Sample Trays 120

(i) Method of Attaching Identifiers Composed of Two-Digit Numerical Values to the Sample Trays 120

As a method of attaching identifiers each of which is composed of a two-digit numerical value to the sample trays 120, the identifiers are attached to the sample trays 120 based on a table 161 as illustrated in FIG. 6 in which the identifiers 164, the types 162 of the sample, and process information 163 about processes are mutually linked.

Herein, the types 162 of the samples include blood serum, blood plasma, and urine; and the process information 163 includes a routine (normal) process, the necessity of a centrifugal separation process, the necessity of decapping, and urgency (priority). The range of the numbers of the corresponding identifiers is described in the region of the identifiers 164.

The table illustrated in FIG. 6 can be optionally set/changed by the operator or a serviceman and is determined in consideration of the circumstances in each test room. For example, in a test room in which the objects to be handled are specialized for blood analysis, all of the vertical parts about "urine" can be set to "0-0" so that only the elements about blood can be selected.

Also, in a test room in which only the samples which have already undergone centrifugal separation are handled, all of the horizontal parts about "routine" are set to "0-0". The range of the values of the corresponding identifiers should be set based on the information of the number of handled samples.

Then, the identifiers and the processing contents are mutually linked, and the contents are registered in the sample test automation system. For example, for the trays of which values of the identifiers are 41 to 49, the processes that skip the centrifugal unit are registered to be carried out since the samples installed thereon have already undergone centrifugal separation. For the trays of which values of the identifiers are 51 to 59, registration is carried out so as to skip the decapping unit since no caps are recapped to the installed samples. The trays of which values of the identifiers are 91 to 99 are STAT samples and registered to be processed as first priority.

The operator is only required to install the samples 150 on the appropriate tray(s) 120 in accordance with the contents set by himself/herself. For example, in the case of the samples 150 of whole blood which are the samples 150 which have already undergone centrifugal separation or the samples 150 which do not require centrifugal separation, the samples 150 are installed on the sample tray 120 of which value of the identifier is 41 to 44. In the case of the samples 150 of urine with no caps, the samples are installed on the sample tray 120 of which value of the identifier is 58 or 59. The STAT samples 150 are installed on the sample tray 120 of which a value of the identifier is in the nineties.

Next, the sample-installed sample tray 120 is set in the tray storage unit 110b, in which no sample tray 120 is installed, in the sample introducing unit 10. A signal that indicates that the sample tray 120 has been set in the sample introducing unit 10 serves as a trigger to start a process.

First, the identifier reading apparatus 111 at the bottom of the tray storage unit 110b reads the identifier of the sample tray 120. Based on contents which have been registered in advance, the sample test automation system 1 recognizes the processing contents of each of the samples 150 according to the information of the read identifier of the tray and positional information of the picked up sample.

For example, the sample 150 picked up from the sample tray 120 of which the identifier is 41 to 44 is processed while skipping the centrifugal unit. The sample 150 picked up from the sample tray 120 of which the identifier is 58 or 59 is processed while skipping the decapping unit. Alternatively, the processing of the sample installed on the sample tray 120 of which the identifier is in the nineties is prioritized over all the others.

When management is carried out in the above-described manner, uniform processes can be carried out without individually inputting the information of the samples to the sample test automation system.

(ii) Method of Attaching Identifiers Composed of Multi-Digit Numerical Values to the Sample Tray 120

As a method of attaching identifiers composed of multi-digit numerical values to the sample tray 120, the identifiers are attached to the sample tray 120 based on a table 170 as illustrated in FIG. 7 in which the types, processes, etc. of the samples are associated with respective digits of the multi-digit numerical values. The example illustrated in FIG. 7 describes an example in which each of the identifiers is composed of a seven-digit numerical value. Details can be set by using the multi-digit numerical value.

Information about the sample is imparted to the numbers of the digits illustrated in FIG. 7. For example, the type of the sample is imparted to a first digit 171, the necessity of a centrifugal process is imparted to a second digit 172, the necessity of a decapping process is imparted to a third digit 173, the necessity of a recapping process is imparted to a fourth digit 174, the information of a conveyance destination is imparted to a fifth digit 175, the information about priority of the processes is imparted to a sixth digit 176, and the information about the shape of the container of the sample (type of the container) is imparted to a seventh digit 177.

These setting items can be optionally selected, contents thereof can be optionally set, and these are determined in consideration of the circumstances in each test room.

Then, the numerical values of the digits of the identifier and processing contents, types, etc. are mutually linked, and the contents illustrated in FIG. 7 are registered in the sample test automation system.

Then, in accordance with the setting contents, the samples 150 are installed on the sample tray 120, which is appropriate. Then, the sample-installed sample tray 120 is set in the tray storage unit 110*b* of the sample introducing unit 10.

When the sample tray 120 is set, the identifier of the sample tray 120 is read through the identifier reading apparatus 111, and this serves as a trigger to start processes. According to the information of the read tray identifier and the positional information of the picked up sample, the sample test automation system 1 can recognize the processing contents based on the above-described contents registered in advance. In this manner, the sample test automation system which carries out appropriate processes for each sample can be provided.

In order to avoid intermediation of human errors of the operator with respect to these operations, a method in which display by characters is added in accordance with needs in addition to symbols of the identifiers is also effective. Coloring the trays is also an effective way to prevent mistakes.

Figure 16:
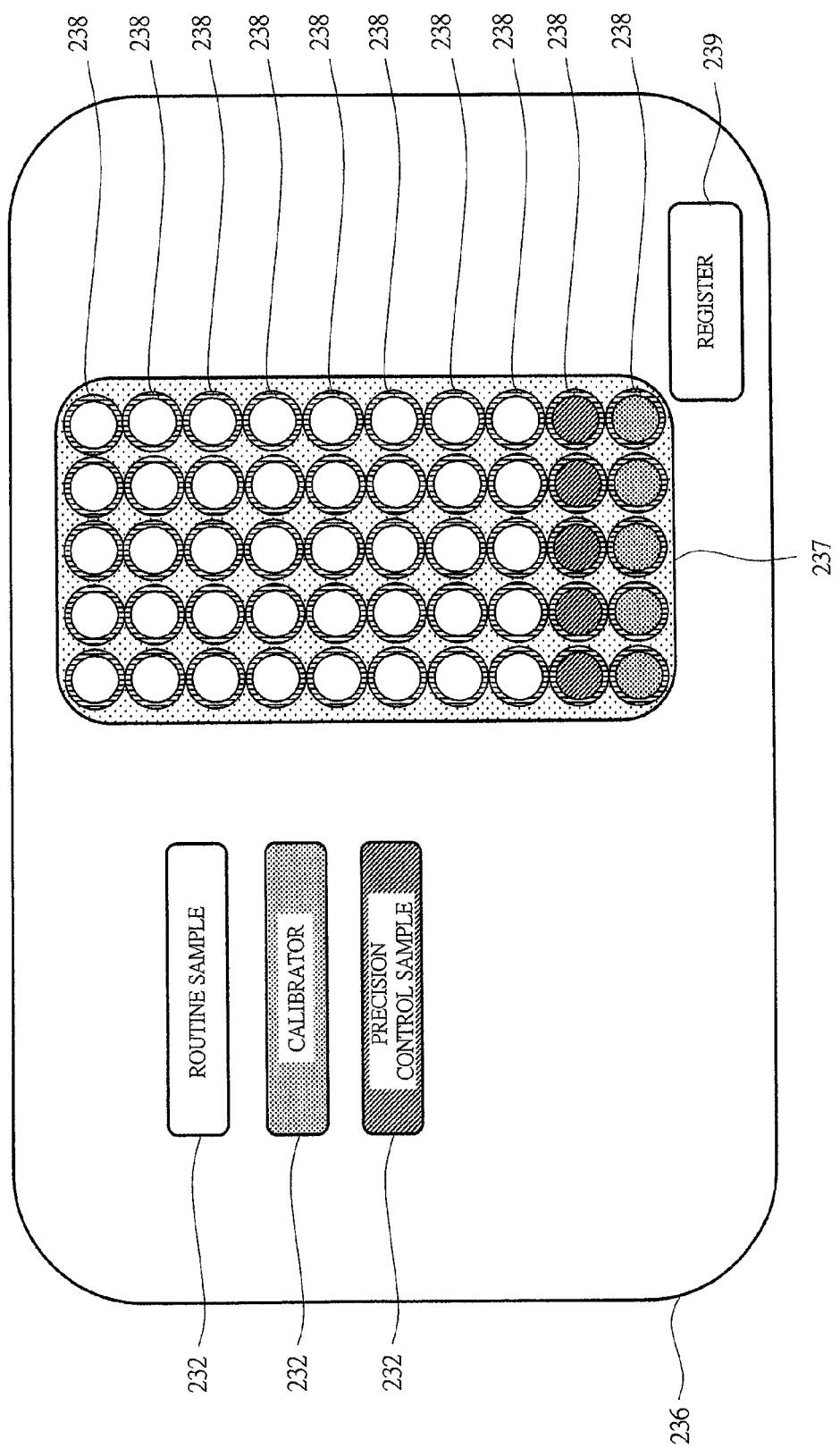
FIG. 16 is a diagram illustrating an example of the tray of the sample test automation system according to the embodiment of the present invention.

Furthermore, other than the specific examples illustrated in FIGS. 6 and 7, a method that incorporates a method in which calibrators and precision control samples for controlling the system are distinguished from routine samples collected from patients is also effective (FIG. 16).

In the case in which samples collected from a single patient with a plurality of blood collection tubes are to be introduced, a method in which a processing course omitting a redundancy check, which is a normal essential function, is provided for the sample of the second tube is also effective. Adopting a mechanism which distinguishes the sample of the second tube from samples of add-on tests is also effective (FIG. 17).

Figure 17:
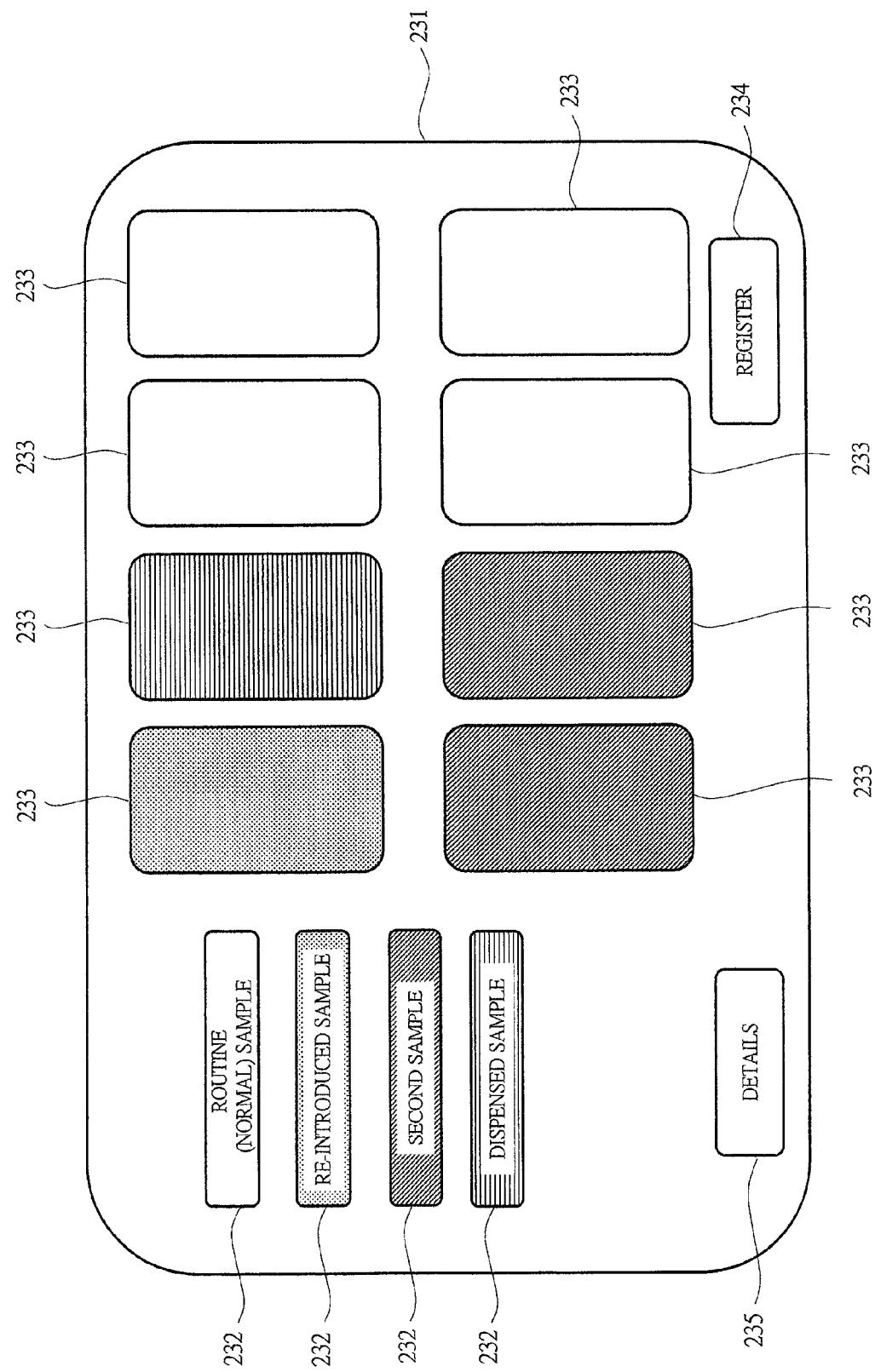
FIG. 17 is a diagram illustrating an example of the tray of the sample test automation system according to the embodiment of the present invention.

Adopting a method which enables introduction of manually-aliquoted aliquot samples directly to the system is also effective (FIG. 17).

(2) Method of Imparting Information to Locations (i) Method of Imparting Information to Disposed Locations of the Sample Trays 120

As a method of imparting information to the disposed locations of the sample trays 120, the installed locations of the sample trays 120 in the sample introducing unit 10 and the processing contents are caused to correspond to each other. For example, as illustrated in FIG. 8, eight tray-disposed locations are compartmentalized into five (181 to 185) regions.

The number of compartments and the areas thereof can be arbitrarily specified in accordance with the corresponding processing contents and the number of processes and should be set in consideration of the circumstances of a used hospital or test center.

Then, the locations of the sample trays 120 and the processing contents are mutually linked and registered. For example, the samples 150 of the type most frequently introduced to the sample test automation system are caused to correspond to a region 181 having the largest area. In fact, a series of processes of separating blood serum from the blood of whole blood collected from patients and aliquoting (separation into small portions) that is a process frequently carried out in many test rooms. The samples 150 set in the region 181 are registered to carry out processes as "routine processes".

In addition, in a large test center that undertakes componential analysis of blood, the samples 150 which have undergone centrifugal separation are sometimes handled. A region 182 serves as a region in which the samples 150 which have already undergone centrifugal separation are set, and the samples placed in the region 182 are registered to skip the centrifugal separation process. Similarly, a region 183 for handling the samples 150 with no caps, a region 184 for handling the samples 150 such as urine other than blood, and a region 185 for handling STAT samples are reserved, and respective processing contents (for example, skipping the decapping unit or processing as first priority) are registered.

The operator is only required to install the samples 150 at appropriate locations on the sample trays 120 in accordance with the contents set by himself/herself. For example, whole blood samples are installed in the region 181, the samples 150 which do not require centrifugal separation are installed in the region 182, no-cap samples are installed in the region 183, urine samples are installed in the region 184, and STAT samples are installed in the region 185, respectively.

The installation of the samples 150 serves as a trigger to start the processes. According to positional information of the sample tray 120 of the picked up sample 150, the sample test automation system 1 recognizes the processing contents of each sample 150 based on the contents registered in advance.

For example, the samples 150 installed on the sample tray 120 of the region 181 are subjected to routine processes. The samples installed in the sample tray 120 of the region 182 skip the centrifugal unit. The samples installed on the sample tray 120 of the region 183 skip the decapping unit. The samples installed on the sample tray 120 of the region 184 are processed as first priority.

Note that the correspondence depending on the types of the samples 150 has been described in this case. However, a different use using differences in the shapes of the caps, differences in the processing contents, etc. as keys may be adopted.

When management is carried out in the above-described manner, uniform processes can be carried out without individually inputting the information of the samples to the sample test automation system.

(ii) Method of Logically Compartmentalizing the Sample Tray 120

As a method of logically compartmentalizing the sample tray 120, the sample tray 120 is logically compartmentalized so that positions thereof correspond to processing contents. For example, as illustrated in FIG. 9, the sample tray 120 is compartmentalized into four (186 to 189).

The number of compartments and the areas thereof can be arbitrarily specified in accordance with the corresponding processing contents and the number of processes and should be set in consideration of the circumstances of a using hospital or test center.

Then, the locations in the compartments in the sample tray 120 and the processing contents are mutually linked and registered. For example, the samples 150 set in a region 1 (186) are registered to be processed as "routine processes". A region 2 (187) serves as a region in which the samples 150 which have already undergone centrifugal separation are set, and the samples placed in the region 187 are registered to skip the centrifugal separation process. Similarly, a region 3 (188) is registered as a region for handling the samples 150 of urine, and a region 4 (189) is registered as a region for handling STAT samples.

When management is carried out in the above-described manner, uniform processes can be carried out without individually inputting the information of the samples to the sample test automation system. More detailed separation can be carried out by further compartmentalizing the sample tray 120 into a plurality of compartments.

In the method of logically compartmentalizing the sample tray 120, the method of imparting the information to the disposed locations of the sample trays 120 may be employed in combination so that the sample trays 120 are logically compartmentalized at particular disposed locations of the sample trays 120.

<3. Setting Screen>

Figure 12:
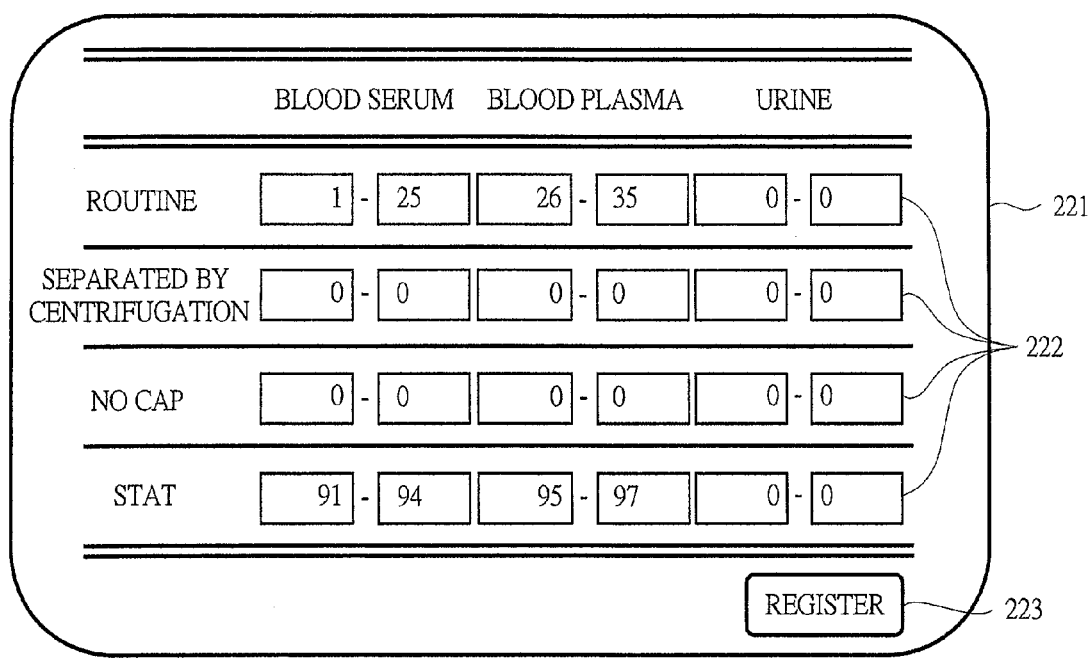
FIG. 12 is a diagram illustrating an example of a third layer screen of the setting screen of the sample test automation system according to the embodiment of the present invention.
Figure 13:
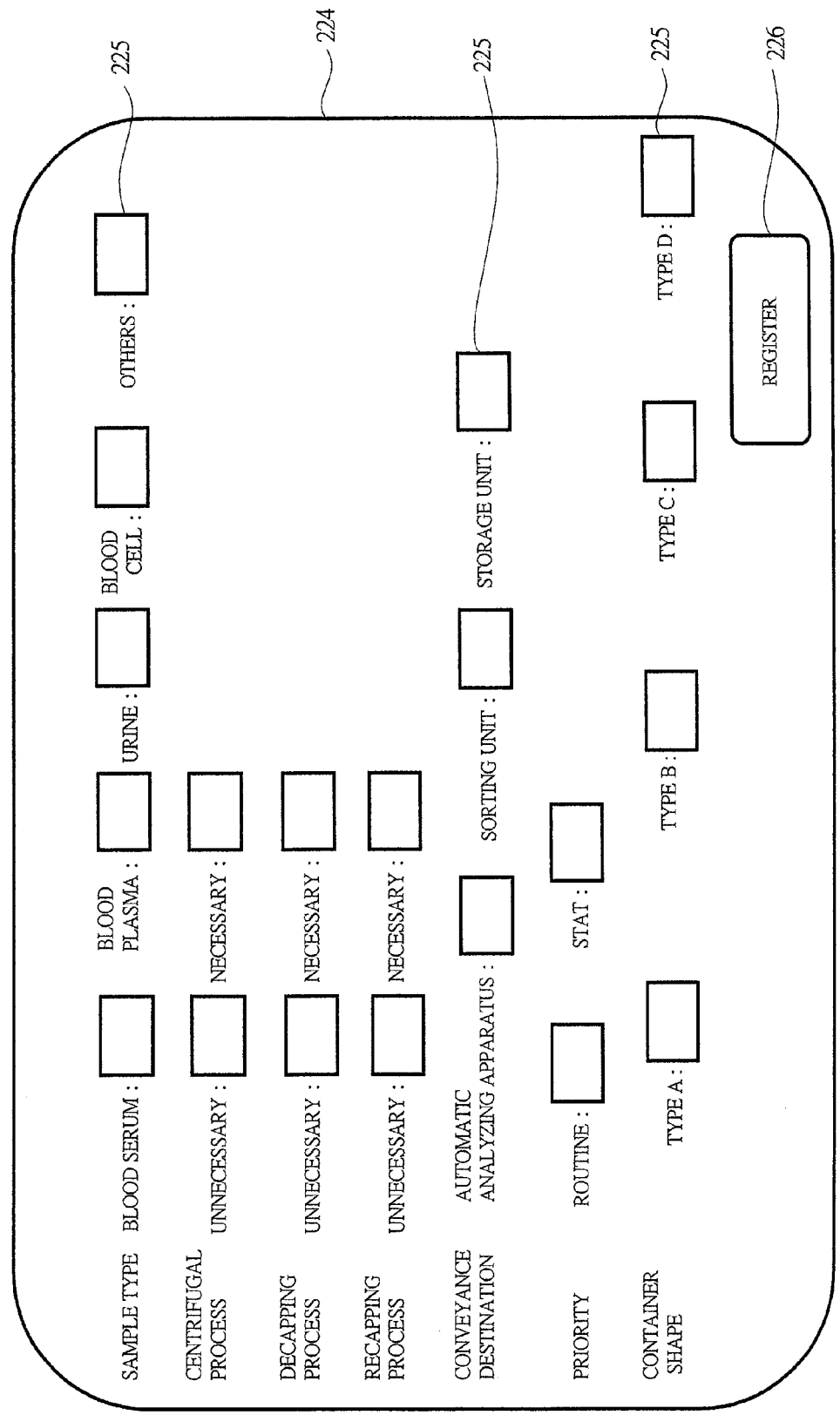
FIG. 13 is a diagram illustrating an example of a third layer screen of the setting screen of the sample test automation system according to the embodiment of the present invention.
Figure 14:
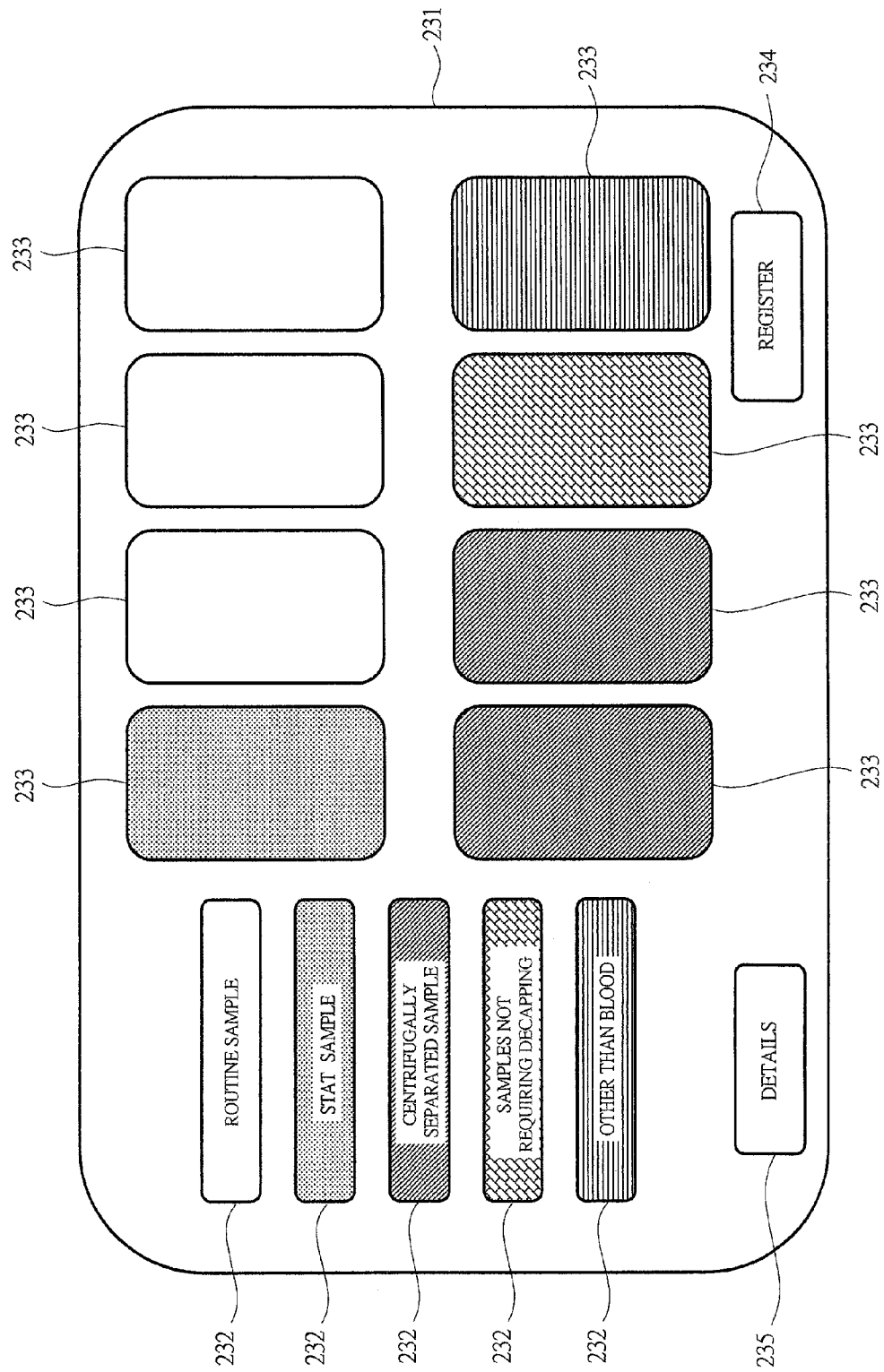
FIG. 14 is a diagram illustrating an example of another second layer screen of the setting screen of the sample test automation system according to the embodiment of the present invention.
Figure 15:
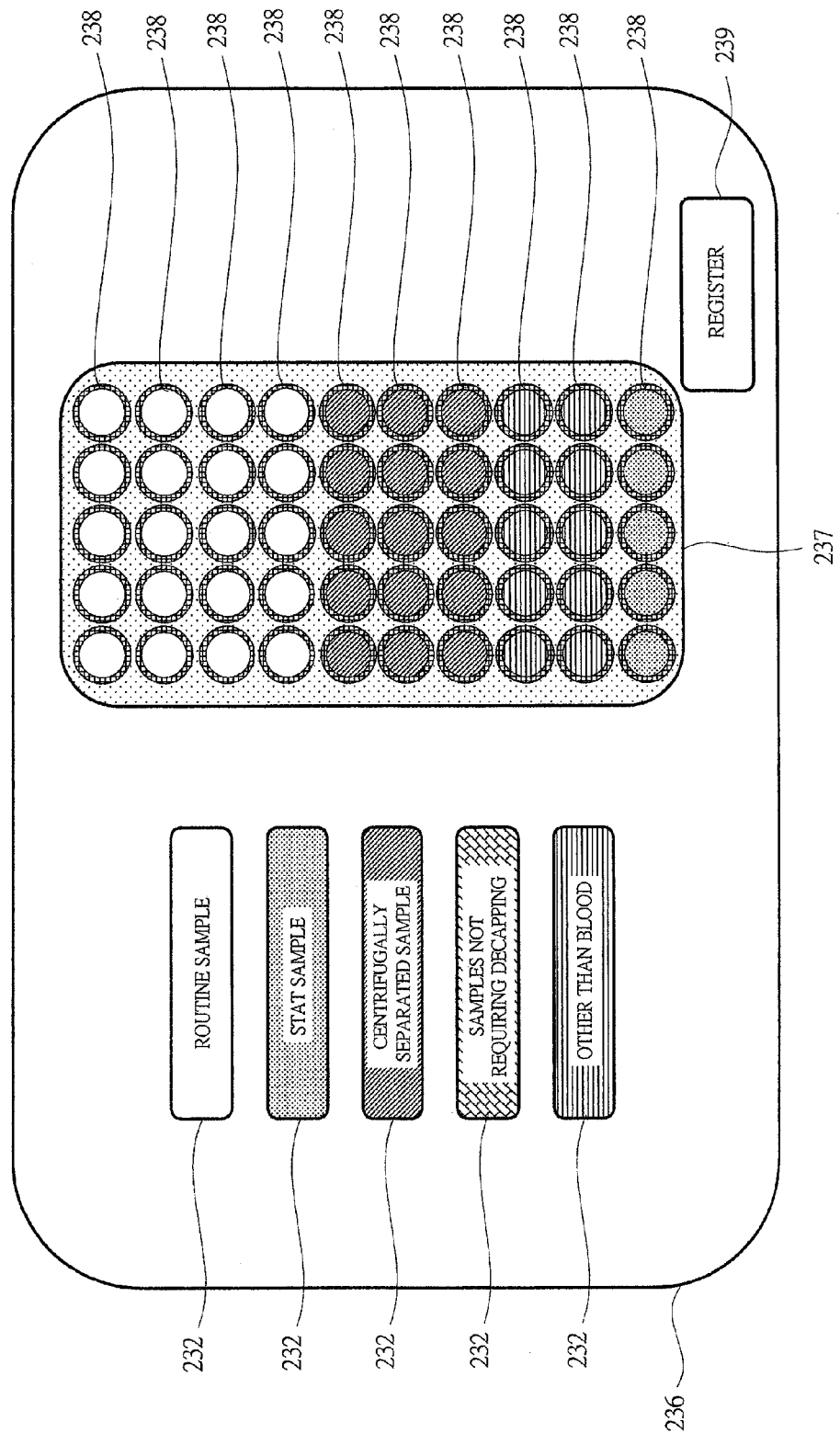
FIG. 15 is a diagram illustrating an example of another third layer screen of the setting screen of the sample test automation system according to the embodiment of the present invention.

Next, examples of setting screens of the sample test automation system according to the embodiment of the present invention will be described with reference to FIGS. 10 to 15. FIGS. 10 to 15 show examples of screens for describing the examples of the setting screens of the sample test automation system according to the embodiment of the present invention. FIG. 10 shows the example of a first layer screen of the setting screen, FIG. 11 shows the example of a second layer screen of the setting screen, FIGS. 12 and 13 show the examples of third layer screens of the setting screens, FIG. 14 shows the example of another second layer screen of the setting screen, and FIG. 15 shows the example of another third layer screen of the setting screen.

The operator can set above-described various contents through the setting screens as illustrated in FIGS. 10 to 15.

First, the setting screen 201 illustrated in FIG. 10 serves as a first layer of the setting screen. The setting screen 201 is composed of a button for imparting the information to the identifiers of the trays ((1) button for selecting the method of attaching the identifiers to the sample trays 120) 202 and a button for imparting the information to the tray disposed positions of the introducing unit ((2) button for selecting the method of imparting the information to the locations) 203.

(i) Selecting the Button 202 for Selecting the Method of Attaching the Identifiers to the Sample Trays 120

When the button 202 is pressed, the setting screen 211 of a second layer of the setting screen as illustrated in FIG. 11 is displayed. The setting screen 211 of the second layer is composed of elements, i.e., an initializing button 212, a setting button 213, a detail button 214, and a table 215 displaying setting contents.

When the initializing button 212 among them is pressed, all of the numerical-value parts of the displayed table are cleared. Then, when the setting button 213 is pressed, the setting screen 221 of a third layer as illustrated in FIG. 12 is displayed.

In the setting screen 221 of the third layer, numerical values can be input via input cells 222 for the contents explained in the above-described method of attaching the identifiers composed of the two-digit numerical values to the sample trays 120. The maximum number of the digits which can be input is adjusted in advance by the scale of a facility which uses the sample test automation system.

After necessary items are input, a registration button 223 is pressed. Then, the information is stored in the sample test automation system, the screen is switched to the setting screen 211 of the second layer illustrated in FIG. 11, and the updated contents are displayed as the table 215.

If the detail button 214 is pressed in the setting screen 211 of the second layer illustrated in FIG. 11, for example, the different setting screen 224 of the third layer as illustrated in FIG. 13 is displayed, and the contents explained in the above-described method of attaching the identifiers composed of the multi-digit numerical values to the sample trays 120 can be set. The numerical values desired to be set are input via input cells 225; and, when a registration button 226 is pressed after input of necessary items is finished, the information is updated in the sample test automation system.

(ii) Selecting the Button 203 for Selecting the Method of Imparting the Information to the Locations When the button 203 is pressed, another setting screen 231 of the second layer as illustrated in FIG. 14 is displayed. In this setting screen 231, the contents explained in the above-described method of imparting the information to the disposed locations of the sample trays 120 are set. The setting screen 231 is composed of buttons 232 for inputting the types of the samples 150, icons 233 of the sample trays 120, a registration button 234, and a detail button 235.

The icons 233 of the sample trays 120 are displayed by the same layout as that of the trays in the sample introducing unit 10. In the present embodiment, the number of the trays in the sample introducing unit 10 is eight, and the eight icons are therefore prepared. When the icon to be selected is selected, it becomes an active state. Then, the button 232 for inputting the type of the sample 150 is selected and pressed. For example, when the leftmost upper tray is to be set for STAT samples, the leftmost upper icon should be made active by clicking, and the STAT sample button (the second top button of the buttons 232) should be pressed.

The set icon is displayed by the same color as that of the button. When necessary input is finished, the registration button 234 is pressed. When the detail button 235 is pressed with respect to the active sample tray 120, the screen is switched to a setting screen 236 of the third layer as illustrated in FIG. 15. In this setting screen 236, the contents explained in the above-described method of logically compartmentalizing the sample tray 120 are set.

Herein, the types of the samples can be registered for all of the sample storage holes 121 by using an icon 237 of the activated tray and icons 238 representing the sample storage holes 121. Each of the holes is made active, and the contents to be set are selected from the buttons 232 for inputting the types of the samples. In this process, in order to reduce redundant operations of the operator, multiple holes can be selected at the same time. In order to reflect the set contents to the sample test automation system, a registration button 239 is pressed.

In the above-described manner, the operator is enabled to easily carry out the setting for which the persons who can carry out the setting have been conventionally limited only to servicemen. The designs of the screens are not limited to those of the setting screens of FIGS. 10 to 15.

Figure 18:
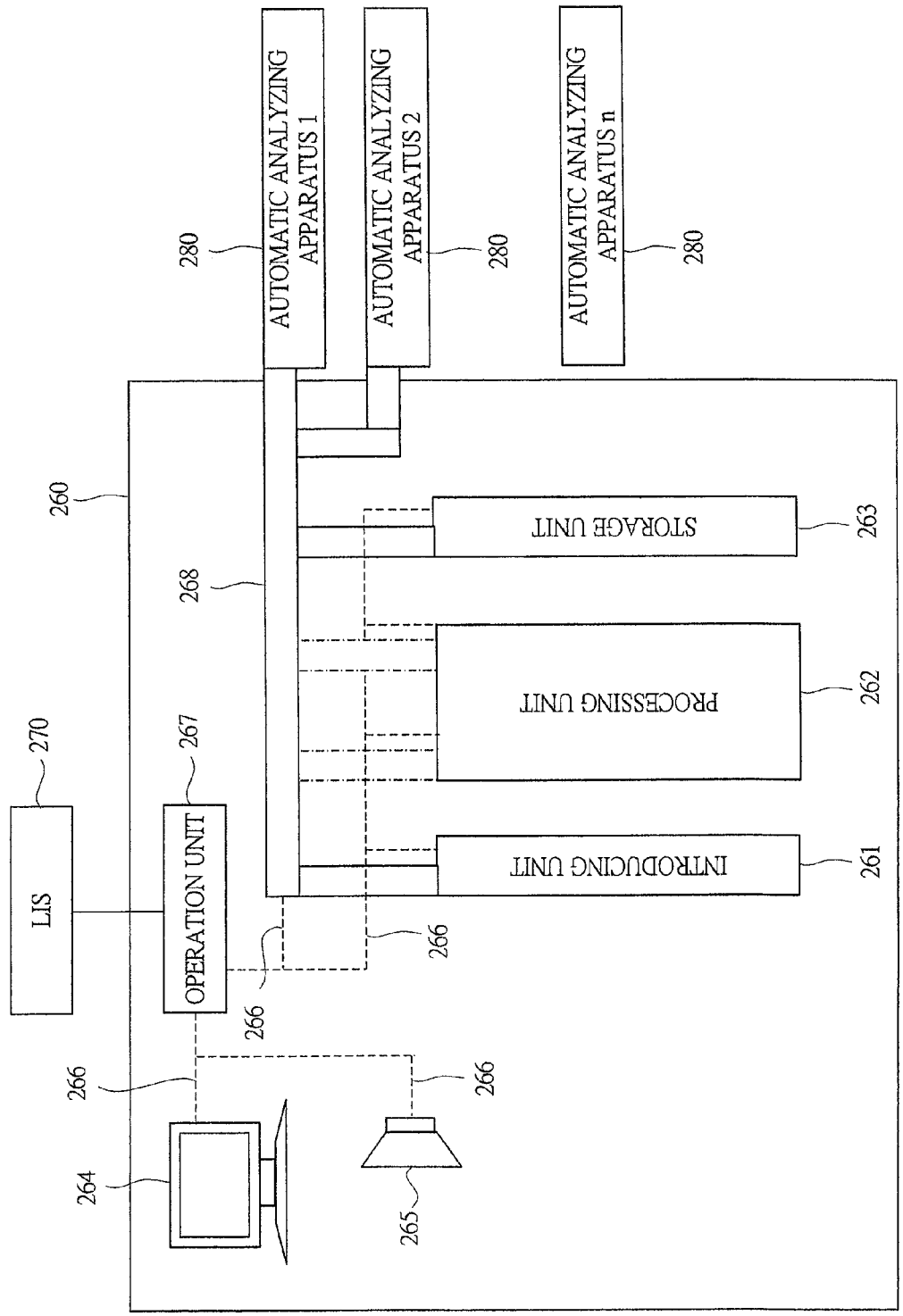
FIG. 18 is a block diagram illustrating a configuration example of an online system adopting the embodiment of the sample test automation system of the present invention.

FIG. 18 is a block diagram illustrating a configuration example of an online system, which adopts the embodiment of the sample test automation system of the present invention.

The online system illustrated in FIG. 18 is provided with automatic analyzing apparatuses 280, which automatically analyze samples, and a sample test automation system 260, which preprocesses samples into modes appropriate for analysis and supplies the samples to the automatic analyzing apparatus 280.

The sample test automation system 260 is provided with: an introducing unit 261; a processing unit 262 illustrated with omitting detailed components; a storage unit 263; an operation unit 267 provided with a monitor 264, a speaker 265, and communication means 266 with the apparatuses; and a conveyance line 268, which conveys the samples from the introducing unit 261 to the processing unit 262, the storage unit 263, and the automatic analyzing apparatuses 280.

The automatic analyzing apparatuses 280 include a model of the mode in which samples are automatically supplied from the sample test automation system 260 by the conveyance line 268 like "AUTOMATIC ANALYZING APPARATUS 1" and "AUTOMATIC ANALYZING APPARATUS 2" in the drawing and a model of the mode in which samples are supplied by manual operation since it is not connected by the conveyance line 268 like "AUTOMATIC ANALYZING APPARATUS n" in the drawing.

The operation unit 267 receives request attribute information from an LIS 270, updates a sample information DB (database), controls the apparatuses by the communication means 266, screen-displays events such as an alarm generated in the sample test automation system by the monitor 264, and notifies test technicians of event occurrence by generating sounds by the speaker 265.

The introducing unit 261 is a module, which introduces a tray on which a plurality of samples to be subjected to preprocessing are installed, and corresponds to an inlet of the online system. Although not illustrated in the drawing, the introducing unit is provided with a mechanism which sets the samples from the tray to a conveyance route. Regarding the samples set to the conveyance route, identification information of the samples is read by an identification information reading means (for example, mainly, barcode reading apparatus), which is not illustrated in the drawing, and is transmitted to the operation unit 267. The operation unit 267 searches the sample information DB whether request attribution information of the samples has already been received or not and transmits arrival information, which indicates whether the request attribute information has already been received or not, to the LIS 270 serving as a high-order system. In the case in which a request has not been made in the operation unit 267 yet, the request attribute information of the sample is transmitted from the LIS 270 to the operation unit 267. When a test item(s) to be preprocessed in the processing unit 262 or a test item(s) to be analyzed and measured in the automatic analyzing apparatus 280 is received according to this request attribute information, the operation unit 267 sends an order to the introducing unit 261 so that the sample is transferred (reformatted) to the conveyance line 268 and conveyed to the processing unit 262.

Although detailed components are omitted in FIG. 18, the processing unit 262 is composed of various processing apparatus in accordance with management needs of test rooms.

Figure 19:
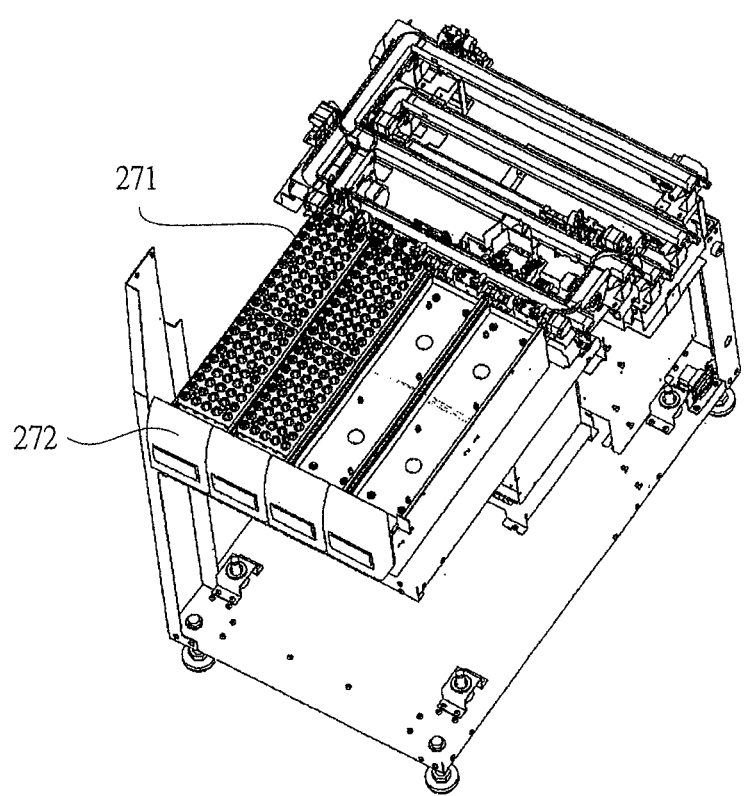
FIG. 19 is a diagram illustrating an internal structure example of an introducing unit and a storage unit.
Figure 20:
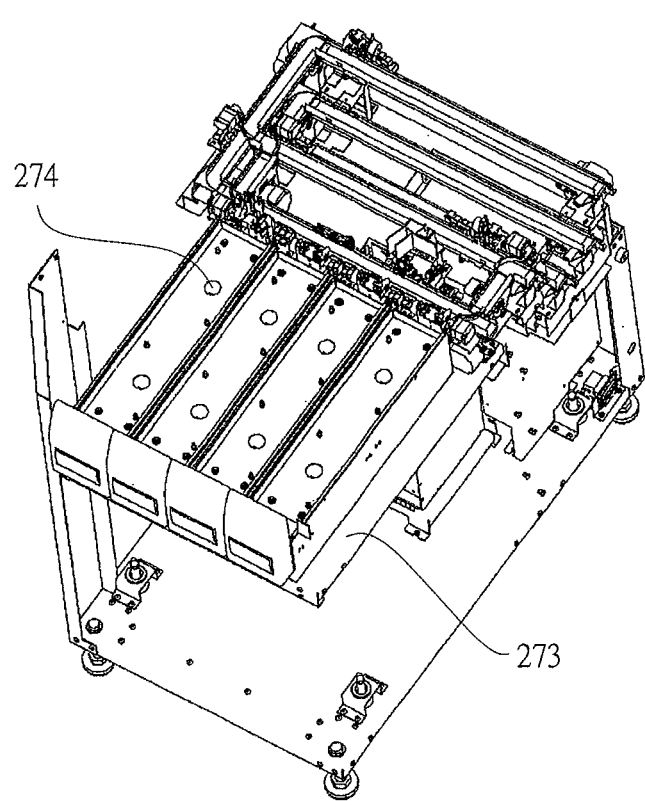
FIG. 20 is a diagram illustrating an internal structure example of the introducing unit and the storage unit.

FIGS. 19 and 20 illustrate internal structure examples illustrating embodiments of the introducing unit 261 and the storage unit 263. The trays 271 are respectively equipped with RFID tags as identifiers (not illustrated), and the trays 271 are configured to be pulled out by sliding to the front side of the apparatus by drawer units 272.

A tray installation base 273 is provided with antennas 274 at each of the positions where the tray 271 is installed and sends/receives information to/from an RFID tag provided on the tray 271. The introducing unit 261 and the storage unit 263 share the trays 271 provided with the RFID tags.

Although not illustrated in the drawings, the storage unit 263 is provided with the mechanism which sets the samples from the conveyance line 268 to the trays 271, and the preprocess-finished samples conveyed to the storage unit 263 are transferred from the conveyance line 268 and installed on the trays 271 installed in the storage unit 263.

The LIS 270 orders an add-on test(s) and addition of a test item(s) for any of the samples installed on the trays 271 of the storage unit 263, and it is transmitted to the operation unit 267 of the sample test automation system 260.

A test technician takes out the tray 271 from the storage unit 263 without changing the state in which the samples are installed thereon. The point when this taking out operation is carried out triggers (for example, the RFID tag is provided on the tray, an RFID antenna is installed in the apparatus side in which the tray is installed, and a state in which the tag starts moving to be separated from the antenna serves as a trigger) the antennas 274 (RFID transmitting/receiving antennas) installed in the storage unit 263 to receive the identification information of the tray 271 from the RFID tag thereof (herein, those including an RFID tag reader are described as an "antenna") and store the information, and, at the same time, the identification information of the taken-out tray 271 is transmitted from the storage unit 263 to the operation unit 267. In the operation unit 267, if it is identified that the samples installed on the tray 271 include the sample (s) for which the add-on test or addition of the test item has been ordered according to the above-described identification information, this is screen-displayed by the monitor 264 to inform the test technician, and sounds are generated by the speaker 265.

The test technician receives the notification generated from the monitor 264 and the speaker 265 and installs the tray 271 in the introducing unit 261 without changing the state thereof. In this process, the antennas 274 installed in the introducing unit 261 read the identification information of the tray 271, the sample(s) for which the add-on test and addition of the test item has been ordered is identified, and only this sample(s) is immediately transferred from the tray 271 to the conveyance line 268.

In some cases, an add-on test (s) and addition of a test item (s) is ordered for the sample(s) of the tray 271 after the tray 271 has been taken out from the storage unit 263. Therefore, the test technician also introduces the trays 271, for which time has elapsed for a while after taking it out from the storage unit 263, into the introducing unit 261 again. However, also in the case in which there is no sample to be transferred again to the conveyance line 268 since it is a tray in which the samples to be subjected to add-on tests and addition of test items are not installed in reality, in the operation unit 267, based on the identification information of the tray 271 transmitted from the introducing unit 261, this is screen-displayed by the monitor 264 for notifying the test technician of this, and also sounds are generated by the speaker 265.

Therefore, there is no need to search at which position in the taken-out tray 271 the sample for which the add-on test or addition of the test item has been ordered is placed, and simplification and authenticity of operations can be ensured.

In this process, it is desired that the screen display and the sounds for notifying that the samples, which are to be re-introduced because of the add-on test and addition of the test items, are installed on the tray 271 when the tray 271 is taken out from the storage unit 263 and the screen display be mutually different type from the sounds for notifying that the samples, which are to be re-introduced because of the add-on test and addition of the test items, are not installed on the tray 271 even when the tray is introduced into the introducing unit 261.

In normal clinical test management, add-on tests and addition of test items should be processed at higher priority than that of first tests (routine samples which are not treated as STAT). Therefore, in the introducing unit 261, the most efficient transfer of the samples to the conveyance line 268 is achieved by cooperation with the operation unit 267 while understanding the introduced state of the samples.

Figure 21:
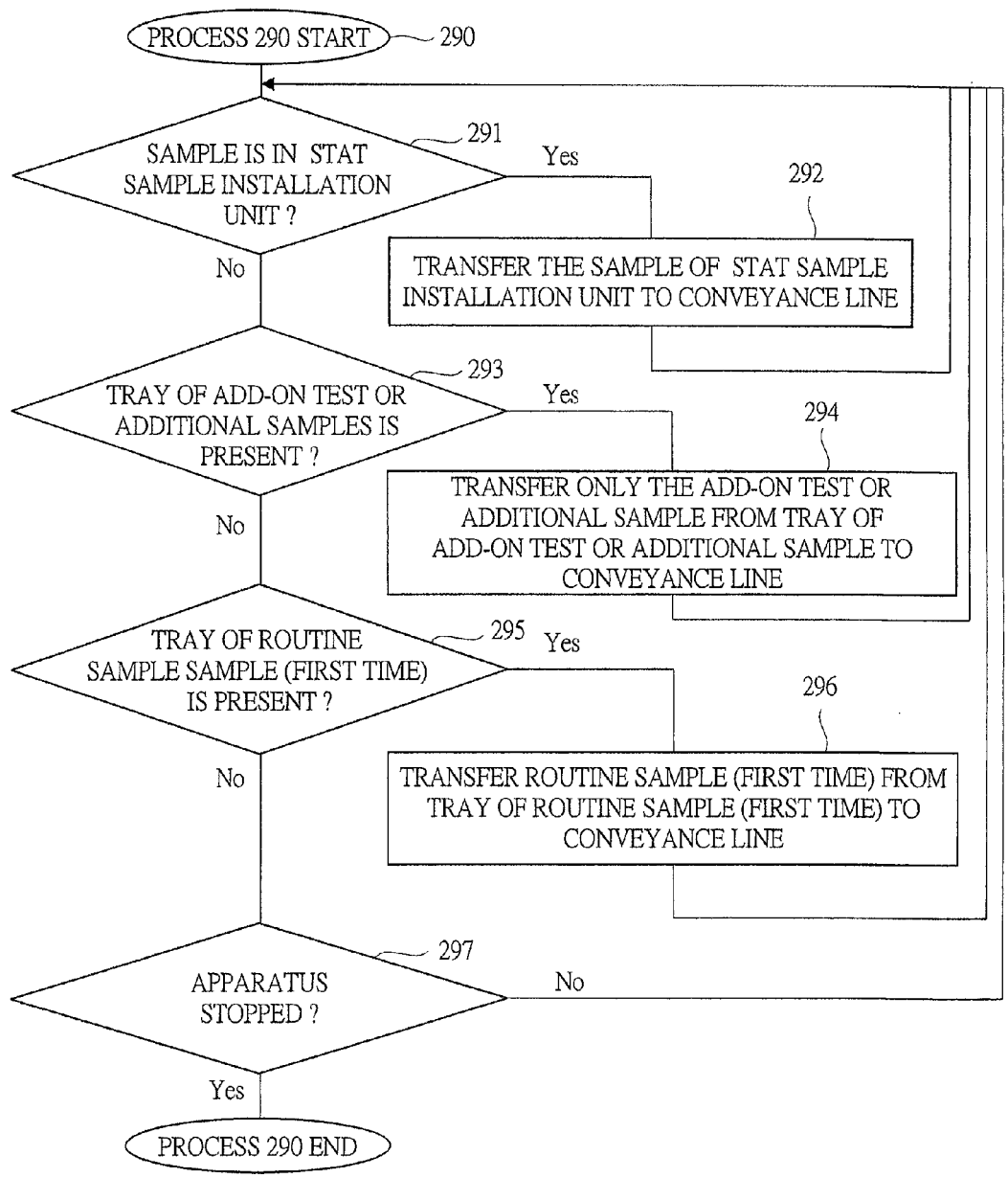
FIG. 21 is a flow chart illustrating a judging process for prioritizing an add-on test or additional test in the introducing unit.

FIG. 21 shows a judging process 290 for achieving the above-described process by the introducing unit 261. Although it is not illustrated in the drawings, other than the locations for installing the trays, the introducing unit 261 is provided with an STAT sample installation unit as a location for installing, by manual operation, the STAT samples for which test implementation is hurried (hereinafter, described as STAT samples) and supplying the samples to the conveyance line 268 in a prioritized manner. The samples installed in the STAT sample installation unit are processed as a first priority; and, after the samples installed in the STAT sample installation unit are eliminated, the process proceeds to a process of transferring (reformatting) the samples from the trays set in a tray installation unit of the introducing unit 261 (steps 291, 292).

The identification information of all the trays and the samples installed on the trays in the introducing unit at this point is comprehensively judged, and a process of transferring only the samples for which add-on tests and addition of test items have been ordered from the trays on which the samples for which the add-on tests and addition of the test items have been ordered to the conveyance line 268 is carried out first (step 293, 294).

Then, a process of transferring routine samples from the trays on which the samples of first tests (routine samples) are installed to the conveyance line 268 is carried out, and the process 290 thereof is repeatedly carried out until the apparatus is stopped (steps 295, 296, 297).

In the above-described embodiment, management of re-introducing the trays 271 from the storage unit 263 to the introducing unit 261 in the single sample test automation system 1 has been described. However, the case in which a plurality of sample test automation systems are controlled by the single operation unit can also employ the management of introducing the trays 271 taken out from the storage unit 263 to the introducing unit 261 of the other sample test automation system mutually among the plurality of sample test automation systems. Also in the case in which operation units are installed in a plurality of sample test automation systems, respectively, similar management can be carried out by carrying out appropriate cooperation among the operation units.

Figure 22:
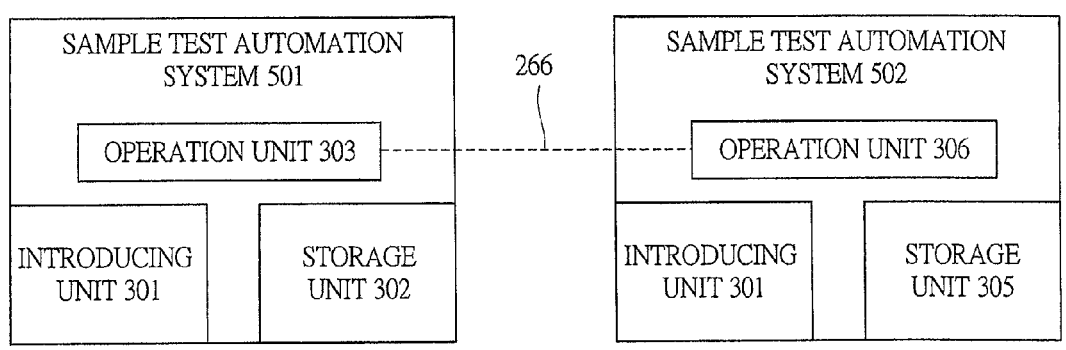
FIG. 22 is a schematic diagram illustrating a cooperation example of a sample test automation system composed of a plurality of systems.

FIG. 22 shows two sample test automation systems 501 and 502. The sample test automation systems 501 and 502 are respectively provided with operation units 303 and 306 and appropriately cooperate with each other by using communication means 266. The tray on which preprocess-finished samples are installed is taken out from a storage unit 302 in the sample test automation system 501 and introduced to an introducing unit 304 of the next sample test automation system 502, thereby carrying out a preprocess to be processed in the sample test automation system 502.

Like this management mode, the system positioned as a second or subsequent system is sometimes referred to as a "postprocess" system since it does not carry out a preprocess.

In the above-described embodiment, passing of the trays among the plurality of sample test automation system has been described. However, also when passing the preprocess-finished tray to a stand-alone apparatus (for example, an automatic analyzing apparatus), an apparatus which reads/writes the identification information is attached to the stand-alone apparatus side so that the information can be passed and the process can be continued.

Examples of the stand-alone apparatus include an aliquoting apparatus which works alone other than the automatic analyzing apparatus.

In another embodiment, generally, one tray on which samples corresponding to a predetermined number of tubes can be installed is used as one sorting destination group in a general example. However, regarding the samples corresponding to a test item for which tests are not frequently requested among the whole processing samples of one day, the number of the samples sometimes does not satisfy the total number of tubes which can be installed on the tray. In such a case, a plurality of positions on the tray are sectioned into particular areas to carry out management of assembling sorting groups.

Figure 23:
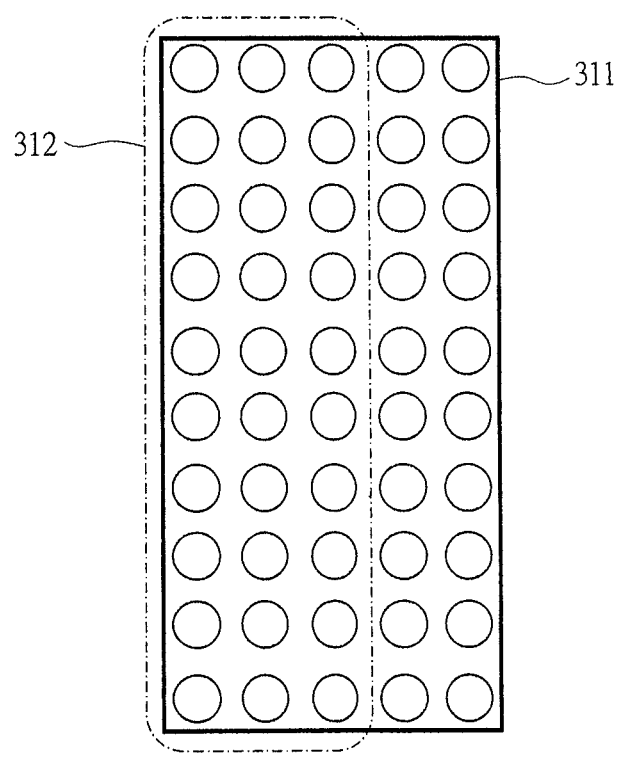
FIG. 23 is a diagram illustrating an example of a state viewing a tray of 5×10 from directly above.

As an embodiment, FIG. 23 illustrates a state in which a tray 311 on which 50 samples can be installed in "5 columns"×"10 rows" is looked down from directly above. As an example of the above-described management, as surrounded by a broken line 312, the left-side three columns are used as one group, and the right-side two columns are used as a sorting destination of another group. When using the management of sectioning a tray into a plurality of areas, management of providing a dedicated tray by carrying out coloring for distinguishing the tray so as to, for example, color the left-side three columns in red and color the right-side two columns in blue in order to facilitate understanding of the test technician and fixing the installation position of the tray in the tray installation base 273 is ubiquitous (assuming management that facilitates a user to understand the installation locations on the tray installation base by coloring and distinguishing the tray side).

Therefore, in the present invention, in the operation unit in advance, sensor position information (sensor is not illustrated in the drawings) indicating tray installation positions on the installation base, tray type information indicating vertical/horizontal sizes of the installed trays, and the range information of identifier numbers (tray IDs) of the trays installed on the sensor positions are set as parameters in the operation unit 267. Then, when the dedicated tray of the test technician is installed in the installation area of the storage unit, rationality check of the identifier of the tray and the above-described parameters is carried out; and, if irrational, alarms are generated by the monitor 264 and the speaker 265 to notify the test technician of the fact that the type of the installed tray and the installation position of the tray are wrong.

FIG. 24 illustrates a display screen example 320 of the above-described parameters displayed by the monitor 264. Although detailed descriptions will be omitted, as shown by a broken line 321, for the installation position at which the sensor position is 8, usage of a divided tray including "3 columns"×"10 rows" and "2 columns"×"10 rows" and the ID range of the tray are set as parameters.

According to another embodiment, the samples collected since a preprocess thereof is interrupted due to some sort of errors are transferred to the trays 271 installed in the introducing unit 261 and the storage unit 263, and the samples are collectively set in individual areas of each tray 271 depending on the substances of the errors.

The substances of the errors include that a state in which re-introduction cannot be carried out before taking out the sample by manual operation and removing, for example, clogging components like an aliquoting error; while an arrival check time-out error sample for which request attribute information has not been transmitted from LIS 270 within determined response time does not require treatment and is in a state the sample can be re-introduced without change.

The samples in the state in which they do not require treatment and can be subjected to retry of re-introduction without change as described above are also collectively transferred to a predetermined area of the predetermined tray 271 set in advance, and the identification information of the samples are stored in the identifier of the tray 271.

When the test technician takes out the tray 271 from the predetermined position of the introducing unit 261 or the storage unit 263 and re-introduces the tray to the introducing unit 261, the samples collected by the arrival check time-out error are transferred to the conveyance line 268 again.

The samples for which the request attribute information has been normally transmitted as a result of the re-introduction described above are subjected to a normal preprocess without change. The samples which undergo arrival check time-out errors again are sorted and separated not into the area of the arrival check time-out errors in the predetermined tray, but into an area in which treatment is not required due to no corresponding request so that re-introduction is not carried out, which is also effective as a management method.

A next embodiment uses management of initializing the information stored in the identifier of the tray 271 to provide a new tray 271 and setting new samples thereon; therefore, the operation unit 267 is provided with a tray information initializing screen 322 as illustrated in FIG. 25. After inputting a number (not illustrated in the drawings) imparted to the used tray 271 to a screen, a user sets new processing samples on the tray 271 and introduces the tray to the introducing unit 261; as a result, the information stored in the identifier of the tray 271 is initialized, and the tray 271 is repeatedly used. Alternatively, all of the processing samples are removed from the tray 271 for which initialization has been ordered by the screen, and the tray 271 is set in the storage unit 263; as a result, the information stored in the identifier of the tray 271 is automatically initialized, and the tray 271 is repeatedly used.

In another embodiment, the identifier of the tray 271 stores the date of the stored date of a primary sample and is provided with parameters for setting a tray expire date in advance; and, in the operation unit 267, optical values for management can be set by a user as the parameters by a tray expire date parameter screen 323 as illustrated in FIG. 26. In the screen example as illustrated in FIG. 26, mutually different expire dates can be set respectively for the tray ID ranges. The tray 271 which has exceeded the tray expire date can be judged to have exceeded the expire date by the number of elapsed days according to the date of storage on the identifier and the current date and by set values of the parameters; as a result, the information stored in the identifier of the tray 271 is automatically initialized.

Since initialization is automatically carried out in this manner, the tray 271 which has been perceived by the user in advance that the expire date has been exceeded can be subjected to the management of installing new processing samples thereon and directly setting the tray to the introducing unit 261 or removing all of the processing samples therefrom and setting the tray to the storage unit 263 without operating the tray information initializing screen 322.

According to another embodiment, the "previously installed location" of the tray 271 is stored in the identifier of the tray 271, the emptied tray 271 installed in the introducing unit 261 and emptied after finishing introducing processing management of samples is treated as "new" when installed in the introducing unit 261 again, the information once stored in the identifier is initialized, and the installation information is then stored again in the identifier. In such an embodiment, regulations in the management are generated so that re-installation to the introducing unit 261 is always treated as "new". As a result of providing such regulations, labor can be saved by automatically initializing the identifiers of the trays 271.

Also, by detecting that no samples are placed on the tray 271 to be installed in the storage unit 263 by using a CCD camera, which is hardware not illustrated in drawings, the information stored in the identifier of the tray 271 can be automatically initialized.

Also, by detecting that no sample is placed on the tray 271 to be installed in the storage unit 263 by using a weight detector, which is hardware not illustrated in the drawings, the information stored in the identifier of the tray 271 can be automatically initialized.

According to the foregoing embodiments of the sample test automation systems, the following effects can be achieved.

The trays are handled in order to minimize the frequency of direct contact between the test technician and the samples. As a result, simple operations are realized, mix-up of samples and delay of test results which are human errors can be prevented, and the risk of infection can be avoided.

Figure 27:
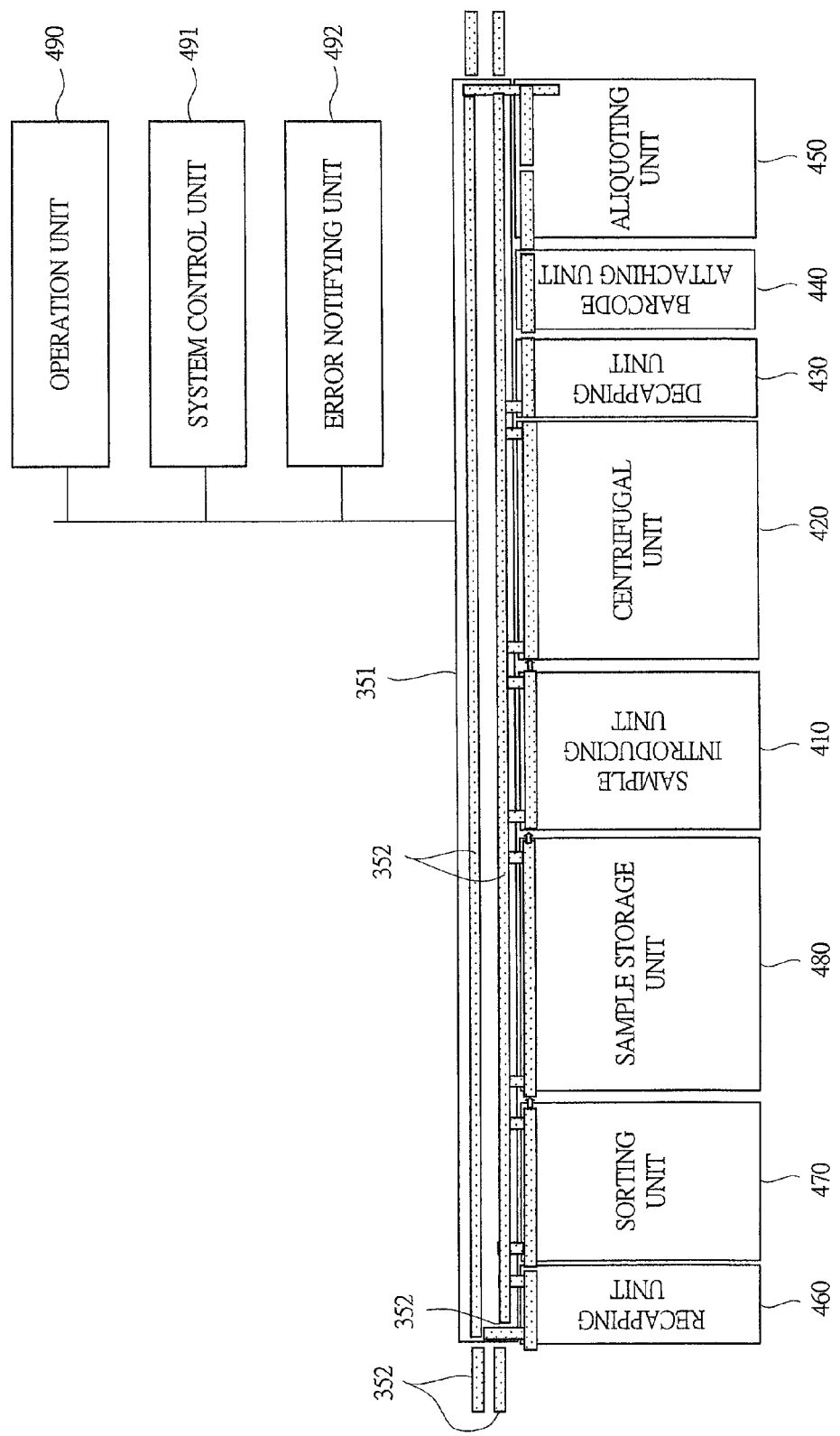
FIG. 27 is an overall schematic diagram of a sample test automation system which is an embodiment of the present invention.

FIG. 27 is an overall schematic diagram of a test sample automation system according to an embodiment of the present invention.

The sample test automation system 351 according to the present embodiment is composed of: a sample introducing unit 410; a centrifugal unit 420; a decapping unit 430; a barcode attaching unit 440; an aliquoting unit 450; a recapping unit 460, a sorting unit 470, a sample storage unit 480; a conveying unit 352, an operation unit 490, a system control unit 491, and an error notifying unit 492.

In this case, after samples are taken into the system from the sample introducing unit 410, the samples stop by at the centrifugal unit 420, the decapping unit 430, the barcode attaching unit 440, the aliquoting unit 450, and the recapping unit 460, and the samples then go to the sorting unit 470 or the sample storage unit 480. If some sort of error occurs in the process of processing the samples, the system control unit 491 perceives this, and the samples are carried out to an error sample carrying-out destination in the system.

In some systems, an analyzing apparatus is connected, and, in that case, part of the samples are conveyed to the analyzing apparatus and subjected to various analytical processes.

The sample test automation system 351 of the present embodiment often is a horizontally-long system, and the length thereof is over ten meters in some cases. Therefore, in a frequently generated operation, the distance of moving is preferred to be as short as possible. The present embodiment is characterized in that, in order to reduce the load of the operator, the carrying-out destination of the error sample can be arbitrarily selected from a plurality of destinations, and the moving distance of the operator is shortened as much as possible.

The sample introducing unit 410 is installed mainly in order to carry in samples from outside mainly into the sample test automation system 351. In this embodiment, the sample introducing unit 410 also has a function of carrying out the samples in the system to outside.

Figure 28:
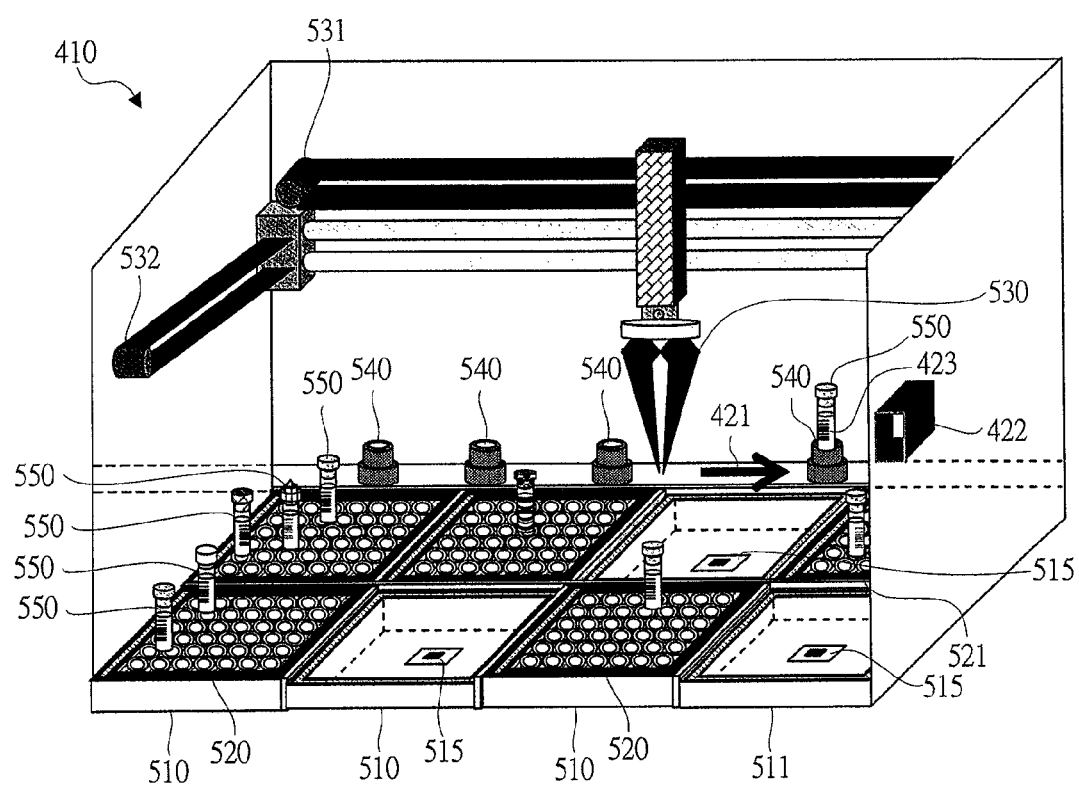
FIG. 28 is a configuration diagram of a sample introducing unit.

A configuration of the sample introducing unit 410 will be explained by FIG. 28.

The configuration is composed of: first sample trays 520 on which sample containers 550, which are to be introduced into the system after this point of time, are collectively installed; first sample tray installation units 510 on which the first sample trays 520 are installed; second sample trays 521 on which sample containers taken out from the system are collectively installed; second sample tray installation units 511 on which the second sample trays 521 are installed; an arm unit 530, which moves the samples from the first sample trays 520 to sample holders 540 and moves the samples from the sample holders 540 to the second sample tray 521; an in-module conveying unit 421, which moves the sample holders 540 from/to the conveying unit 352; and a sample identifier reading unit 422, which reads identifiers 423.

Figure 32:
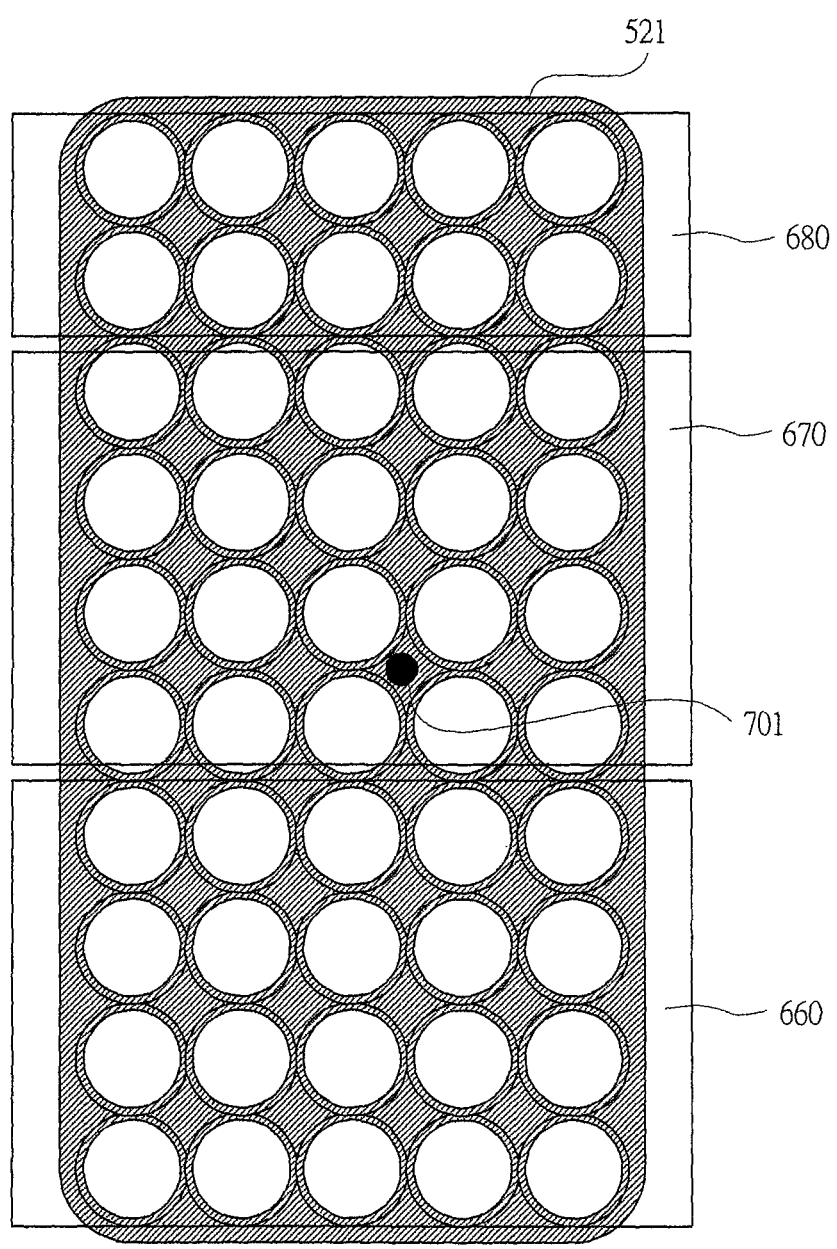
FIG. 32 is a diagram illustrating an example of the carrying-out destinations of the error samples in a sample tray according to FIG. 30.
Figure 36:
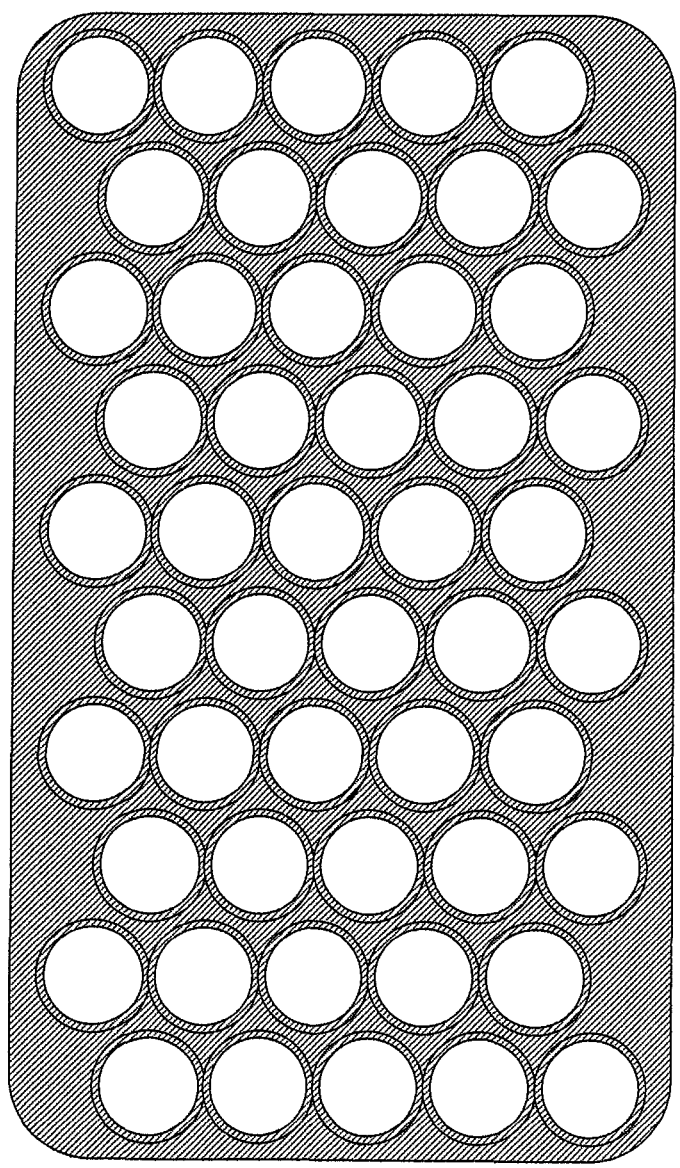
FIG. 36 is a diagram illustrating an example of the sample tray of a layout in which holes are shifted by one column or one row.

Both of the first sample trays 520 and the second sample trays 521 are supporters for retaining the samples, and holes for retaining the samples are disposed in a plurality of columns. FIG. 32 shows an example of the sample tray on which holes are arranged like a lattice of n-rows and m-columns. FIG. 36 shows an example of the sample tray of an arrangement in which each column or each row of the holes is shifted. This case can be treated by a similar idea as that of the lattice-like sample tray by considering the zigzag-arranged holes as one row or one column; therefore, hereinafter, the lattice-like sample tray will be taken as an example to explain. Each of the holes is present for inserting the sample container, and the inserted sample is maintained substantially upright without falling down. Each of the holes is configured so that a normally-used test tube having a diameter of 9 mm to up to 17 mm can be maintained upright, and even sample containers having different diameters can be installed on the single sample tray.

The first sample trays 520 can be removed from the sample introducing unit 410. The first sample tray 520 is convenient for collectively installing about several tens or several hundreds of sample containers 550, which are to be processed after this point of time, on a working table in a test room.

The operator places the first sample tray 520 near a reception location of a test room, and the samples of which reception checking operation has been finished are sequentially set on the first sample tray 520. At a point when a certain amount of samples are stored, the operator sets the first sample tray 520 to the first sample tray installation unit 510 of the sample introducing unit 410.

Then, the arm unit 530 holds and lifts up the container sequentially from the sample container 550 installed on either one of the back side or front side of the first sample tray 520 seen from the operator and moves and installs the sample to the sample holder 540 waiting on the in-module conveying unit 421.

The identifier 423 for distinguishing from other samples is attached on the sample container 550. The sample identifier reading unit 422 reads the identifier 423 attached on the sample container 550 when the sample holder 540 passes the vicinity of the sample identifier reading unit 422.

At this point, a situation that the identifier 423 of the sample cannot be read due to some sort of error occurs. If the identifier 423 of the sample is a barcode label, for example, taint of the barcode label, defective printing, defective attaching such as tilted attaching or partial peel-off, or forgotten attaching is conceivable. In this case, the system control unit 491 cannot judge what kind of process should be carried out for the sample container 550. Therefore, the system control unit 491 recognizes the sample container 550 as an error sample and conveys the sample to a location different from that of normal samples.

The operator has to carry out a recovery process for continuing the process of the error sample. The operator prints/creates the identifier 423 of the sample again by a barcode printer, pastes that on the sample container, and introduces the sample again from the sample introducing unit 410 into the system.

Based on the information of the read identifier 423 of the sample container 550, the system control unit 491 has to judge and determine which processing module the sample should stop by and what kind of process should be carried out. For this purpose, the system control unit 491 obtains information about the sample from a test room information system while using the identifier information of the sample as a key. However, a situation that the information about the sample cannot be obtained due to some sort of error can occur. An example thereof is a situation in which reply of the information in the test room information system side is not on time, and time-out occurs. In that case, the system control unit 491 recognizes this sample as an error sample and conveys the sample to a location different from that of normal samples.

One of recovery processes of such an error sample is to re-introduce the sample again from the sample introducing unit 410 after the operator inputs information about the sample from the operation unit 490. Another method is to introduce the sample again from the sample introducing unit 410 at the point when a measure against the error can be taken on the test room information system side.

Then, the sample is conveyed to the centrifugal unit 420 via the conveying unit 352. The centrifugal unit 420 subjects the sample to a centrifugal separation process. The centrifugal unit 420 is composed of: a first sample holder buffer for standby of a sample holder which is waiting for the centrifugal separation process; a centrifugal bucket, in which the sample to be subjected to centrifugal separation is installed; a second sample holder buffer for standby of an empty sample holder for installing the sample of which centrifugal separation process has been finished; and a centrifugal arm unit for moving the sample.

One of the errors that could occur herein is centrifugal interruption. Some sort of error occurs in the system side, and the centrifugal separation process is interrupted in coordination with that. In that case, the system control unit 491 recognizes this sample as an error sample and conveys the sample to a location different from that of normal samples. A recovery process for such an abnormal sample is to judge necessity of centrifugal separation by the operator and subject the centrifugal-required sample to a centrifugal separation process manually. The operator introduces the processed sample again from the sample introducing unit 410.

Then, the sample is conveyed to the decapping unit 430 via the conveying unit 352. The decapping unit 430 is installed to automatically remove a cap, which is attached in order to protect the sample, so that various processes can be carried out in various processing units stopped by after the decapping unit 430.

One of the errors that could occur herein is decapping failure. This is a case in which a decapping process cannot be carried out well due to some sort of cause that, for example, slippage occurs when the cap is to be held or the cap per se is broken. In that case, the system control unit 491 recognizes this sample as an error sample and conveys the sample to a location different from that of normal samples. A recovery process for such an error sample is that the operator subjects the sample to a decapping process by manual operation. The operator introduces the processed sample again from the sample introducing unit 410.

Then, the sample is conveyed to the aliquoting unit 450 via the conveying unit 352. Aliquoting refers to an operation of separating a sample in one primary sample container into small portions in a plurality of sample containers and is normally carried out by using a pipetter. Herein, the primary sample container is referred to as a first sample container, and the sample containers serving as destinations of separation into small portions are referred to as second sample containers. The aliquoting unit 450 automatically subjects the single and plurality of second sample containers to an aliquoting process from the sample in the first sample container in accordance with an order from the system control unit 491.

The second sample containers include sample containers of a test tube type normally having a height of about 70 mm to about 105 mm, a cup type having a height smaller than that, and sample containers of a bottom-raised test tube type having an outer shape like a test tube having a height of about 70 mm to 105 mm and having a container bottom higher than that of a normal test tube. If the second sample container is the test tube type or the bottom-raised test tube type, normally, an identifier such as a barcode is printed and attached by the barcode attaching unit 440 around the aliquoting process so that the sample can be identified in the automatic analyzing apparatus side.

One of the errors that could occur herein is aliquoting failure. The aliquoting failure is that the ordered amount of the sample cannot be aliquoted to the second sample container due to deficiency of the sample per se in the first sample container or influence of foreign matters in the sample. In that case, the system control unit 491 recognizes the sample as an error sample and conveys to a location different from that of normal samples. The second sample containers related to the first sample container are collectively conveyed to the same location. A recovery process for such an error sample is that the operator carries out an aliquoting process by manual operation. The operator introduces the processed sample again from the sample introducing unit.

Furthermore, one of the errors that could occur herein is an identifier error. The identifier error is failure of preparation of the identifier to be attached on the second sample container, which is a barcode label in this case. Normally, conceivable examples include failure of barcode printing, tearing of barcode label paper, and attaching failure. In that case, the system control unit 491 recognizes this sample as an error sample and transfers the sample to a location different from that of normal samples. A recovery process for such an error sample is that the operator prints and pastes a barcode label by manual operation. The operator introduces the processed sample again from the sample introducing unit 410. Another method is to introduce the original first sample container again from the sample introducing unit 410 to start over including aliquoting. The operator carries out the recovery process in either method.

Then, the sample is conveyed to the recapping unit 460 via the conveying unit 352. The recapping unit 460 automatically recaps a cap to the sample container and protects the sample from evaporation and impurity contamination.

One of the problems that could occur herein is recapping failure. This corresponds to a situation in which a recapping process cannot be carried out well due to some sort of cause such as slippage of a cap or breakage of the cap per se. In that case, the system control unit 491 recognizes this sample as an error sample and conveys the sample to a location different from that of normal samples. A recovery process for such an error sample is that the operator subjects the sample to a recapping process by manual operation. The operator introduces the processed sample again from the sample introducing unit 410.

Then, the sample is conveyed to the sorting unit 470 via the conveying unit 352. Sorting refers to an operation of rearranging the samples depending on the purpose of usage or the destination.

An overview of the sorting unit 470 is illustrated in FIG. 29.

The sorting unit 470 is composed of: the in-module conveying unit 421, which conveys the sample-installed sample holders 540 from the conveying unit 352 into the module; the second sample trays 521, on which the plurality of sample containers are collectively installed; the sample tray installation units 511 on which the plurality of second sample trays 521 are installed; the arm unit 530, which moves the samples from the sample holders 540 to the second sample trays 521; and an identifier reading unit 515, which automatically reads the identifiers attached to the second sample trays 521.

The second sample tray 521 can be detached from the sorting unit 470. The plurality of sample containers 550 can be installed on the second sample tray 521, wherein about several tens to several hundreds of samples can be collectively installed. Before starting operation, the operator sets the second sample tray 521, on which no sample is installed, in the second sample tray installation unit 511.

In the sorting unit 470, when the sample that requires sorting flows at the conveying unit 352, the system control unit 491 conveys the sample holder 540 thereof from the conveying unit 352 into the module via the in-module conveying unit 421.

The arm unit 530 holds and lifts up the sample on the sample holder 540 and moves the sample to one of the plurality of second sample trays 521. The second sample tray, which is the move destination, is determined in accordance with the parameters set by the operation unit 490.

This sorting operation is repeatedly carried out until the second sample tray 521 becomes full. When the tray becomes full of samples, an alarm is generated to urge the operator to replace the second sample tray 521. The foregoing description is the explanation of normal operation of the sorting unit 470.

Next, a situation in which the sorting operation fails due to some sort of error will be explained. One of the errors that could occur herein is failure of the sorting operation. Examples of the failure of the sorting operation include that the arm unit 530 fails to hold the sample. In that case, the system control unit 491 recognizes this sample as an error sample and conveys the sample to a location different from that of the normal sample. A recovery process for such an error sample is to introduce the sample again from the sample introducing unit after the operator removes the cause of the sorting operation failure or to carry out the sorting operation per se by the operator instead of the apparatus.

Then, the sample is conveyed to the sample storage unit 480 via the conveying unit 352. This state occurs only when the sample has not been sorted by the sorting unit 470.

Storage refers to the operation of rearranging the process-finished samples depending on the types of the samples and carrying-out/storing the samples to the sample trays. The configuration of the sample storage unit 480 is basically the same as that of the sorting unit 470. A difference is that more second sample trays 521 serving as the carrying-out destination of samples can be installed than in the sorting unit 470, the sample storage unit 480 can retain the second sample tray 521 corresponding to one thousand samples in total while the sorting unit 470 retains the second sample trays 521 corresponding to several hundreds in total.

The outline of the processes of the samples has been explained above. It has been described therein that the sample recognized as the error sample is conveyed to the location different from that of normal samples, and details thereof will be explained subsequently.

First, in the present embodiment, in the sample introducing unit 410, the first sample tray 520 for introducing the sample from outside the system to inside the system can be utilized as the second sample tray 521 for taking out the sample from inside the system to outside the system. Both of these have the same shape and can be mutually replaced. More specifically, when the sample tray is set in the first sample tray installation unit 510 of the sample introducing unit 410, the sample tray functions as the first sample tray, i.e., a sample tray for carrying-in; and, reversely, when set in the second sample tray installation unit 511, the tray functions as the second sample tray 521, i.e., a sample tray for carrying-out. Furthermore, the sample tray installation units can be also switched by parameter setting of the operation unit 490 and can be utilized as the first sample tray installation unit 510 for carrying in the samples and also as the second sample tray installation unit 511 for carrying out the samples. In a test room having a high demand for the processing ability thereof, in which samples are desired to be collectively introduced at one time, all of the sample tray installation units are set as the first sample tray installation units 510. Reversely, when the processing ability is not required so much, part of them is set as the second sample tray installation unit 511 to take out error samples to the sample introducing unit 410; as a result, re-introduction of the samples after error recovery processes can be carried out on site.

In the sample test automation system 351 of the present embodiment, the second sample tray installation units which carry out the samples in the system to outside the system are present in the sample introducing unit 410, the sorting unit 470, and the sample storage unit 480. Not only normal samples but also error samples can be carried out.

The error sample carrying-out destination can be set for each type of the errors and each method of the recovery processes.

As already described, there are several types of the error samples, and the methods of the recovery processes are different depending on the types of the errors. When the error samples are carried out to one location, the operator can collectively process them; on the other hand, it is not known in some cases that what kind of errors happened to the samples and what kind of recovery processes have to be carried out. In that case, the operator has to carry out recovery processes after seeing, on the screen of the operation unit or a record file, what kind of processes should be carried out for which sample; resulting in an inconvenience. Therefore, the present embodiment provides a method by which the operator can collectively carry out operations at one location and can perceive what kind of process should be carried out only by seeing the samples.

In the present embodiment, the carrying-out destinations of the error samples are specified to different locations, i.e., the sample trays or regions in the sample trays respectively for the types of the errors. Furthermore, what kind of error samples are to be carried out is stored in advance in the carrying-out destination by means of, for example, characters or colors which can be distinguished by the operator. As a result, the operator is enabled to perceive the type of the error from the conveyed location and judge what kind of operation should be carried out to carryout the recovery processes without seeing the screen or record file.

Furthermore, another example is a method in which the carrying-out destinations of the error samples are specified respectively for the method of the recovery processes instead of the types of the errors. In this case, if the recovery process methods are the same even in the errors of different types, the operator is not required to distinguish the error samples; therefore, the purpose to enable the recovery processes without seeing the screen or record file can be achieved.

Options for setting the carrying-out destinations of the error samples will be described below.

One of them is the unit of the second sample tray installation unit 511. Several tens of samples can be collectively taken out to the second sample tray 521. A large amount of reset samples are generated at one time after forcible stop of the apparatus occurs; therefore, it is convenient to take out such samples. If necessary, the carrying-out destination of the error samples of the same type can be specified for the plurality of second sample tray installation units 511 so that the error samples can be carried out across to the plurality of second sample trays 521.

Another one is to logically fragment the second sample tray 521 so that the carrying-out destinations of the error samples can be specified in the position units in the tray. In this case, the setting contents of the parameters are the second sample tray installation unit 511 and the positions in the second sample tray 521 installed therein.

In the setting screen of the operation unit 490, information of four types is associated to specify error conveyance destinations. The four types of information are: error-sample type information for specifying the types of the error samples, error-sample carrying-out-destination module information for specifying the modules serving as the carrying-out destinations of the error samples, sample tray installation unit information for specifying the carrying-out-destination sample tray installation unit in the module, and positions in the error-sample carrying-out-destination sample tray. FIG. 30 shows an example of setting in which carrying-out destinations are specified for the types of the error samples, respectively.

Figure 31:
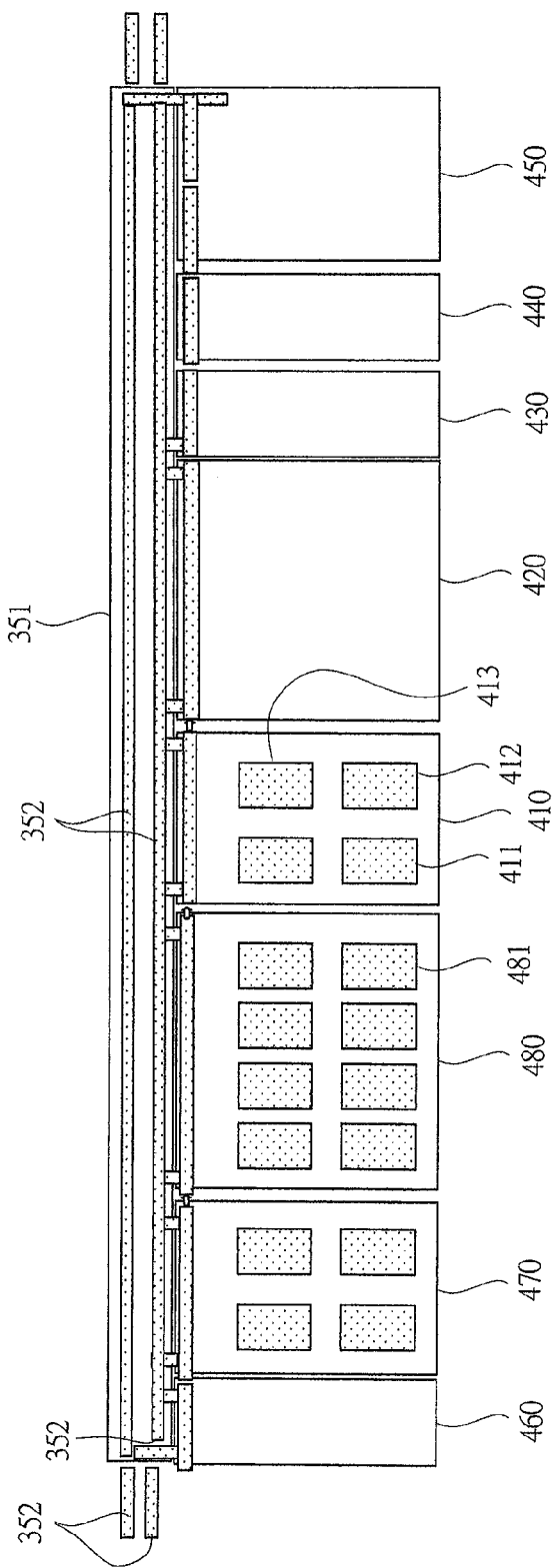
FIG. 31 is a diagram illustrating an example of carrying-out destinations of the error samples according to FIG. 30 illustrated in a whole system.

FIG. 31 shows the carrying-out destinations of the error samples according to the setting illustrated in FIG. 30.

Among the samples for which errors have occurred, the samples of sample-identifier unreadable 210, sample-information unobtainable 220, and decapping process failure 240 are carried out to the sample tray for carrying out error sample, i.e., the second sample tray 521 installed on a sample tray installation unit 413 of the sample introducing unit 410.

Among the error-occurred samples, the samples of aliquoting failure 250 are carried out to the sample tray for carrying out error sample, i.e., the second sample tray installed on a sample tray installation unit 412 of the sample tray introducing unit 410.

Among the error-occurred samples, the samples of centrifugal separation process interruption 230 are carried out to the sample tray for carrying out error sample, i.e., the second sample tray installed on a sample tray installation unit 481 of the sample storage unit 480.

All of them are positioned near a sample tray installation unit for sample introduction, in other words, a first sample tray installation unit 411 and are at the positions from which re-introduction can be easily carried out after error recovery processes are finished.

FIG. 32 shows details of the second sample tray 521 to which the samples of the sample-identifier unreadable 210, the sample information unobtainable 220, and the decapping process failure 240 are carried out. Based on the information set in FIG. 32, the system control unit 491 carries out the error samples to the second sample tray 521 set in the second sample tray installation unit 413 of the sample introducing unit 410.

The second sample tray 521 is a sample tray having holes for inserting sample containers in 5 rows and 10 columns. The tray has sample container installation holes at 50 locations in total starting from the right bottom of FIG. 32 and ending at the upper left of FIG. 32.

A first region 660 has test-tube installation holes at positions 1 to 20, and only the samples of the sample-identifier unreadable 210 are installed therein.

A second region 670 has test-tube installation holes at positions 21 to 40, and only the samples of the sample-information unobtainable 220 are installed therein.

A third region 680 has test-tube installation holes at positions 41 to 50, and only the samples of the decapping process failure 240 are installed therein.

An embodiment about replacement of the second sample tray 521 serving as the carrying-out destination of the error samples will be described below.

An identifier 701 is attached on the second sample tray 521. The identifier 701 is read by the identifier reading apparatus 515 at the point when the second sample tray 521 is set to the second sample tray installation unit 511 and is transmitted to the system control unit 491. Based on this information, after replacement of the second sample tray 521, the system control unit 491 judges how samples are remaining on the second sample tray 521.

A first method will be described. In the system control unit 491, based on the last initialization of a database about the sample trays or the point of time when date is changed, if the identifier 701 of the second sample tray 521 is the identifier read first time thereafter, it is judged that an empty second sample tray from which all samples have been removed is installed, and samples are carried out from the first position. Reversely, if an identifier which has once recognized is read, it is judged that the second sample tray 521 which has been used once is installed again, and samples are sequentially installed thereon from a position on the sample tray next to the position from which the sample has been carried out the last time. Conceiving the case in which the same sample tray has to be used several times, a sample-tray reset ordering unit is provided on the operation screen or near the second sample tray. When this is implemented, the system control unit 491 judges that the second sample tray has been emptied and forcibly carries out samples from the first position.

A second method will be described. In a certain second sample tray installation unit 511, the identifier 701 of the second sample tray is different before and after replacement of a second sample tray 300, the system control unit 491 judges that all the samples on the second sample tray have been removed and carries out the samples from the first position. Reversely, if the identifier 701 is the same before and after replacement of the second sample tray 521, it is judged that the same second sample tray has been installed, and the samples are sequentially carried out from the position next to the position where the sample was previously placed last time. Also in this case, similarly, conceiving the case in which the second sample tray of the same identifier has to be used several times, the sample-tray reset ordering unit is provided on the operation unit screen or near the second sample tray. When tray reset is implemented, the system control unit 491 judges that the second sample tray has been emptied, and the samples are forcibly carried out from the first position.

These two methods are embedded in the system control unit 491 in advance so that they can be switched in the operation unit.

Notification of error occurrence will be described.

The sample test automation system 351 of the present embodiment is provided with the error notifying unit 492, which notifies the operator of occurrence of errors. Conceiving that the operator is not always near the sample test automation system 351, a method capable of giving a notification to a distant location by a sound outputting device or alight outputting device is preferred as a communication means. The errors of the processes with respect to the samples occur in the processing units as described above, and carrying-out destinations of the error samples can be selected from a plurality of locations for the convenience of the operator. Therefore, the location of error occurrence and the carrying-out destination of the error sample are not always close to each other. For example in the aliquoting error, it is a case in which the sample of the aliquoting error is carried out to the sample introducing unit although the aliquoting error has occurred in the aliquoting unit 450.

In this case, a time lag of about several tens of seconds may be generated before the sample is carried out to the error carrying-out destination after the error has actually occurred. If the error notifying unit 492 immediately notifies the operator of the error at the point when the error occurred, a situation occurs in which the error sample has not been carried out yet even when the operator rushes to the carried-out location of the error sample. In this case, the operator has once turned off the alarm and waits on site until the sample comes out or starts another task. If the other task has been started, start of a process may be delayed without noticing carry-out of the error sample since the alarm has been turned off.

In order to avoid this, in the present embodiment, the timing of error notification is at the point when the error sample is carried out to the second sample tray 521 instead of at the point of error occurrence. The point of carrying-out referred to herein includes over ten seconds around the point.

Furthermore, in this embodiment, the timing of alarm generation can be set from the operation unit 490. Options of the timing of alarm generation are immediately after the error occurrence or at the point when the error sample is carried out to the second sample tray 521.

Furthermore, conceivable units of the alarm for which the alarm generating timing can be set are three types including the unit for all alarms and units which can be separately set for each alarm or for each alarm of which recovery process method of error samples are the same.

A method of causing the sample test automation system 351 to carry out a process of a case when failure occurs again after an error has occurred will be described.

Basically, if a process fails, the sample test automation system 351 of the present embodiment carries out the failed sample to outside of the system, and the operator manually carries out the process. When the sample is carried into the system again, the sample test automation system resumes the process that is subsequent to the failed process. For example, the processing units are sequentially arranged in the order of the sample introducing unit 410, the centrifugal unit 420, the decapping unit 430, the aliquoting unit 450, and the sample storage unit 480; and, in a case in which processes thereof are to be sequentially carried out, if an error occurs in the centrifugal unit 420, the operator manually carries out a centrifugal process for the sample, and, after re-introduction, the sample test automation system continues the process from that of the decapping unit. However, in a situation in which a centrifugal separation process has not been carried out almost at all since an error occurs for some reason immediately after centrifugal separation is started, the operator may judge that the centrifugal process can be carried out again in the sample test automation system. This system provides means for forcibly carrying out the previously failed process again in such a case.

A method to achieve this is a method that provides the first sample tray 520 for forcible re-processing or the first sample tray installation unit 510. All of re-introduced samples carried-in therefrom are configured so that the process thereof is started again from the error-termination-occurred process. This method is convenient in a case in which re-processing is collectively ordered at one time since there is no need to repeatedly specify re-processing for any of the samples from, for example, the operation unit screen. Particularly, several tens of error samples are generated at one time in the above-described recovery process after interruption of the centrifugal separation process; therefore, the present method is effective.

Another method to realize this is a method of providing a re-processing forcible ordering unit on the screen of the operation unit 490. After the identifiers of the samples which are desired to be re-processed are specified on the operation unit screen, re-processing is ordered from the re-processing forcible ordering unit. Then, when samples are introduced, the re-processing is carried out only for the specified samples. This method is convenient for re-processing errors of a small number of samples caused by individual errors depending on the samples. Examples thereof include a case in which aliquoting fails in the aliquoting unit since foreign matters such as fibrin have precipitated in the sample.

The ways of arranging the error samples which have undergone aliquoting failure in the aliquoting unit 450 will be described.

In the sample test automation system 351 of the present embodiment, if an error occurs upon aliquoting, the aliquoting process is interrupted, and the sample is returned to the first sample container which is a source thereof. At most ten second sample containers, which are the destinations of separation into small portions, can be generated in accordance with an order from the test room information system side; and, if aliquoting fails, all of them become empty. Furthermore, even in the case in which aliquoting fails, the barcode labels serving as the identifiers are attached on the second sample containers. On the identifier attached on the second sample container, the ID for specifying the sample, a sample ID, the amount of sample aliquoting, destination, and what analysis it is to be utilized are printed. This indicates that how much samples have been supposed to be aliquoted into the second sample container if aliquoting is normally carried out. This supports the operator to carry out aliquoting by manual operation by seeing the numerical values thereof in the process of a recovery process of aliquoting failure without seeing the screen of the operation unit or printed matter.

When the system control unit 491 recognizes occurrence of aliquoting failure, the first sample container, which is the source, and all of the second sample containers related thereto or all of the aliquoting-failed second sample containers are conveyed to an error-sample conveyance destination. Whether the conveyance targets for the error-sample conveyance destination are to be all of the second sample containers or the aliquoting-failed second sample containers can be also set from the operation unit 490. In the error-sample conveyance destination, the first sample containers and the second sample containers are arranged on the second sample tray 521 in the manner illustrated in FIG. 33.

Figure 33:
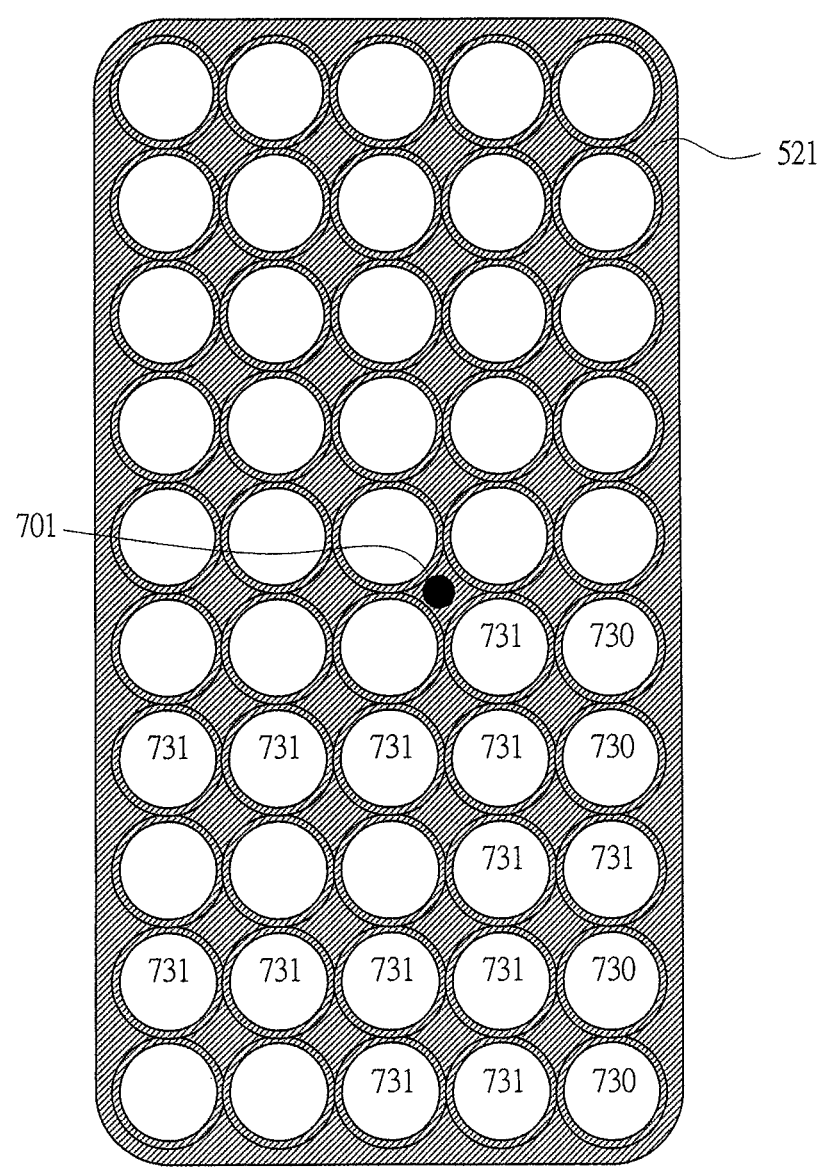
FIG. 33 is a diagram illustrating an example of carrying out an error sample upon aliquoting failure.

FIG. 33 shows a state in which aliquoting-failed samples are arranged on the second sample tray 521. The second sample tray has holes arranged in a lattice of 10 rows and 5 columns, and sample containers can be inserted therein, respectively. In this case, in total 50 sample containers can be installed on the second sample tray 521. Each of the holes is configured to retain a normally-used test tube having a diameter of 9 to 17 mm upright, and even sample containers having mutually different diameters can be carried out onto the single second sample tray. The first sample containers and the second sample containers are often mutually different types; therefore, it is essential that the test tubes having mutually different diameters can be installed on the single sample tray.

First sample containers 730 serving as aliquoting sources and second sample containers 731 serving as destinations of separation into small portions are arranged as illustrated in FIG. 33 according to rules described below.

One of the rules is that the containers of the first sample and the second sample are carried out to mutually adjacent positions. First, aliquoting failure occurs with respect to a certain sample, and there is a necessity of carrying out one first sample container and two empty second sample containers related thereto to the second sample tray. In this case, the first sample container is carried out to the first column of the first row. Furthermore, the two second sample containers are carried out to the second and subsequent columns in the same row as the first sample container without space therebetween. In this case, the containers are carried out to the second and third columns.

If the number of the second sample containers exceeds "the number of columns −1", the second sample containers are arranged from the first column of the next row. If the number of the second sample containers is 6, the fifth and sixth second sample containers are arranged in the first column and the second column of the next row of the primary sample.

Another one of the rules is that, if the first sample containers serving as sources are different, the first sample containers are carried out to mutually different rows. If aliquoting failure newly occurs and the first sample container and the second sample containers related thereto are to be carried out, the containers are carried out after switching to the next row even if vacant positions are still remaining in the row to which the sample container has been carried out last time. The way of arrangement upon carry-out has a rule similar to that of the previous samples.

According to the above-described rules, first, the carrying-out destinations are separated depending on the types of errors in the present embodiment; therefore, the operator can recognize that the carried-out samples are those of aliquoting failure according to the carried-out location. Furthermore, the first sample container serving as a source is always present in the first column, and the empty sample containers serving as destinations of separation into small portions are collectively arranged in one location. Therefore, the operator can easily find the first sample container and the second sample containers which are related to each other.

Furthermore, the aliquoting amount that has to be aliquoted from the first sample container to the second sample container by manual operation is printed on the identifier attached on the second sample container; therefore, after recognizing occurrence of an error by sound or light and rushing to the sample carried-out location, the operator can immediately start a recovery operation on site without seeing a screen or a record file.

Furthermore, the second sample tray, which carries out aliquoting failed samples, and the first sample tray, which re-introduces the samples after recovery processes, are set so as to be positioned close to each other; as a result, the operator is not required to move but can re-introduce the samples on the site.

If a plurality of aliquoting failed samples are collectively present, the second sample tray to which the aliquoting failed samples have been carried out can be detached, and the samples can be collectively processed on a working desk. Also in this case, operation can be carried out without seeing a screen or a record file; therefore, operation efficiency is also good.

A method of efficiently sharing one carrying-out destination by two different types of samples will be described.

The second sample tray serving as a carrying-out destination has holes arranged like a lattice having n-rows and m-columns, and sample trays are inserted thereinto, respectively. Two types of samples, i.e., first-type samples and second-type samples are carried out to the second sample tray for carrying out samples. The first-type samples are carried out to the second sample tray sequentially from the front row thereof, and the second-type samples are carried out to the second sample tray sequentially from the back row thereof. The sample of the first type and the sample of the second type are installed until they are next to (adjacent to) each other, and the installation regions thereof are dynamically changed. Depending on changes in the situation of the test room, the number of each type of the samples is increased/decreased. In this method, the second sample tray can be maximally effectively utilized in any situation.

Furthermore, improvement methods of the present embodiment will be described.

In the previous example, the second sample tray can be maximally utilized; however, since the boundary thereof is not clear, if there is no clear method to distinguish the two types of samples such as different colors of caps or different shapes of sample containers, the operator cannot easily judge where the boundary is. Therefore, in a modified embodiment, instead of installing the first-type error samples and the second-type error samples until they are adjacent to each other, the samples are installed until they are adjacent to each other with one or more holes for installing the samples or one or more vacant rows provided therebetween. At the point when the samples that exceed this condition are delivered, the sample test automation system gives a notification by some method that the sample tray has become full to urge the operator to replace the tray. Even if the shapes of the sample containers of the first type and the second type are the same and cannot be distinguished from each other, the operator can judge the vacancy as the boundary.

Figure 34:
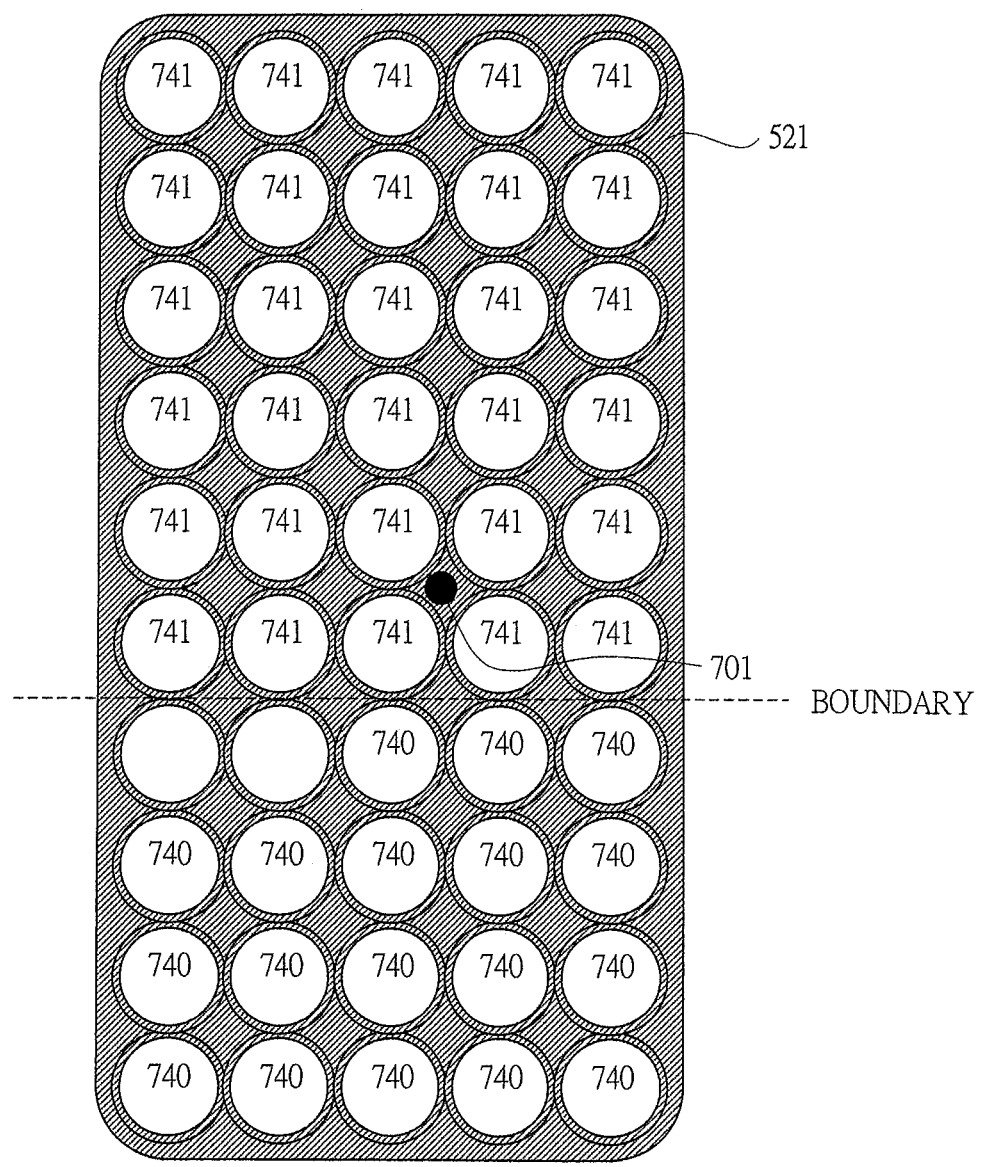
FIG. 34 is a diagram illustrating Example 1 in which two different types of samples dynamically share the sample tray.
Figure 35:
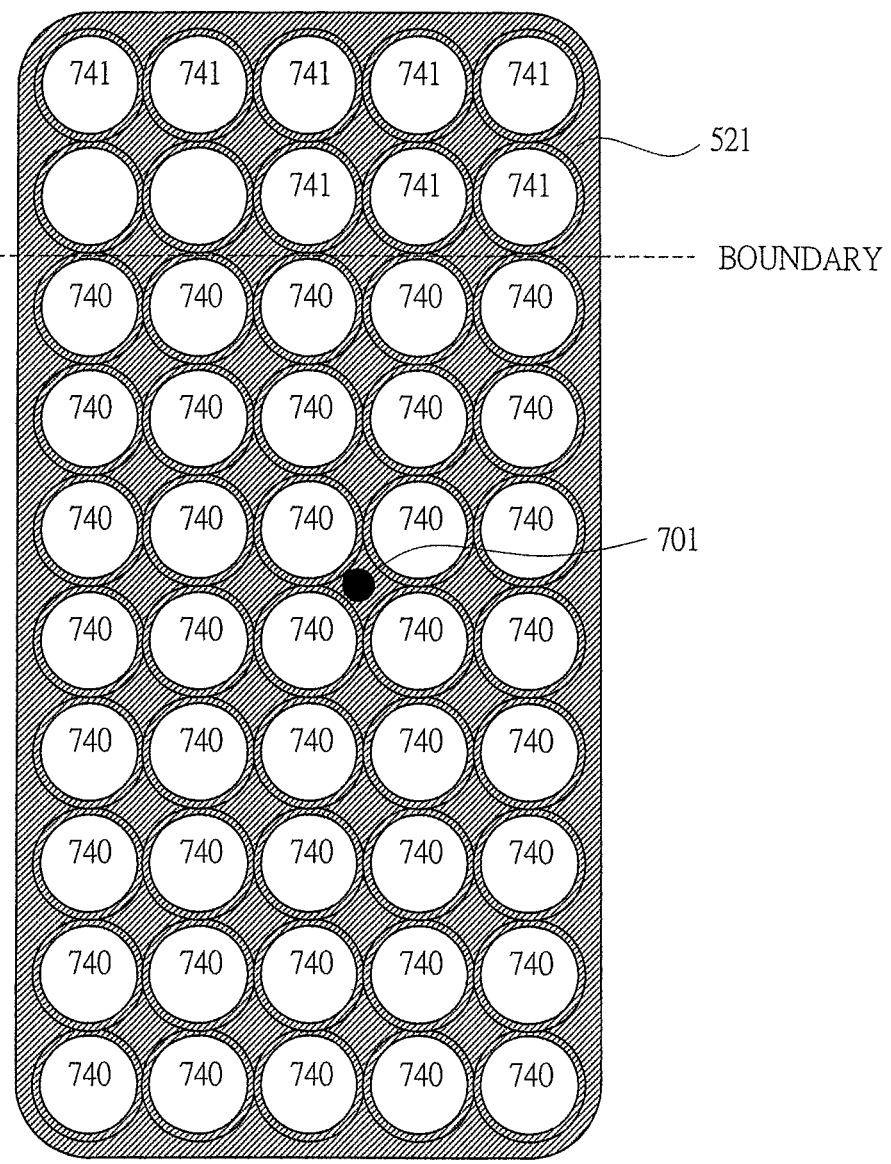
FIG. 35 is a diagram illustrating Example 2 in which two different types of samples dynamically share the sample tray.

FIG. 34 shows a case in which many first-type sample containers 740 have been sorted, and FIG. 35 shows a case in which many second-type sample containers 741 have been sorted. It can be understood that the boundary is dynamically changed to sort more samples both in the case in which the number of the first-type sample containers 740 is large and the case in which the number of the second-type samples is large.

Figure 37:
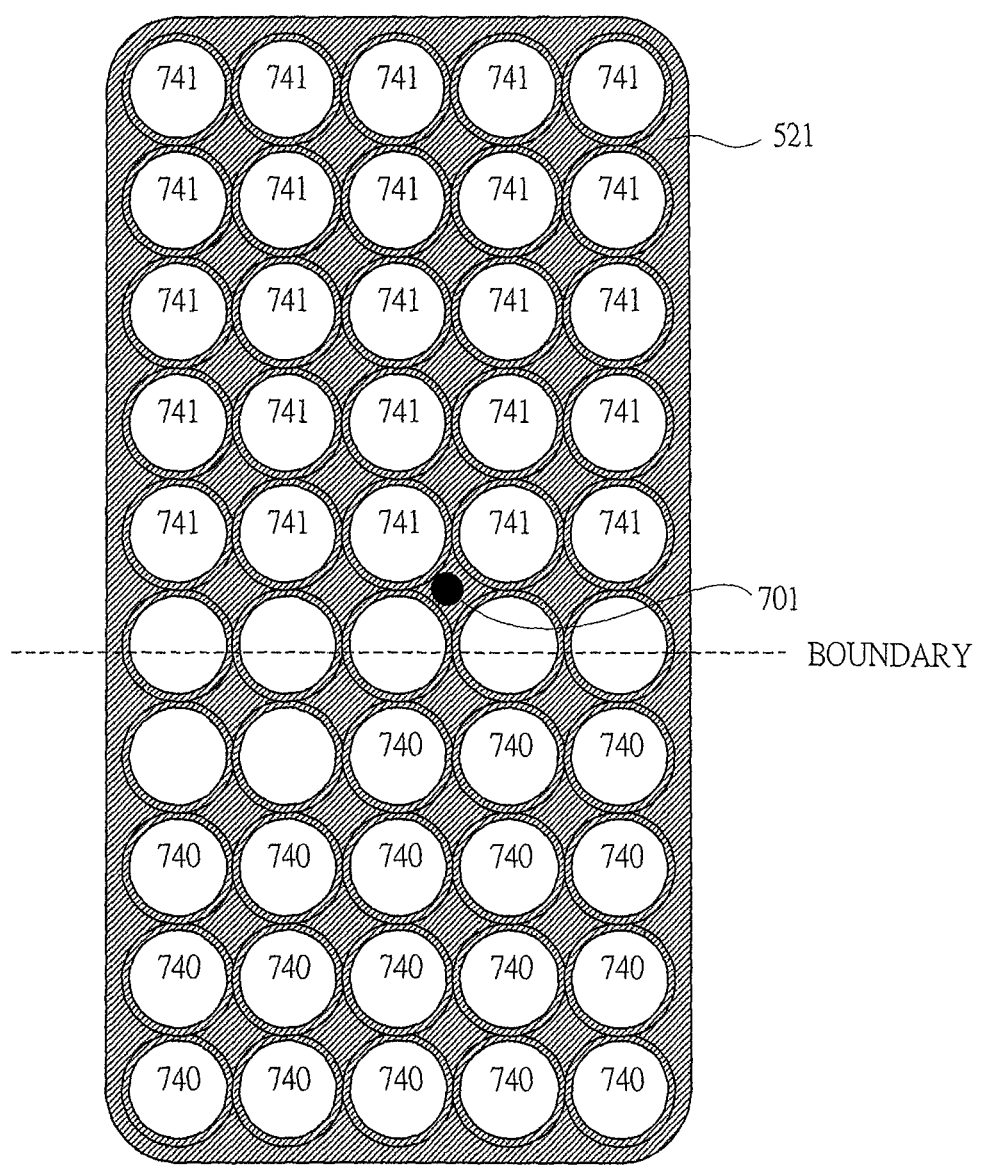
FIG. 37 is a diagram illustrating an example in which two different types of samples dynamically share the sample tray with one or more columns interposed therebetween.

FIG. 37 shows an example in which the first-type sample containers 740 and the second-type sample containers 741 are installed until they are adjacent to each other with one vacant row provided therebetween. In this state, if the next second-type sample containers 741 arrive, the condition that "they are adjacent to each other with one vacant row provided therebetween" cannot be satisfied. At the point when the next second-type sample containers arrive, an alarm indicating that the sample tray has become full is generated to urge the operator to replace the sample tray.

The above-described first-type sample containers can be sorted as error samples, and the second-type sample containers can be sorted as normal samples; and the first type and the second type can be sorted by the types of errors. Also, the samples which require add-on tests can be sorted as the first type, and the samples which do not require add-on tests can be sorted as the second type. The way of sorting of these can be determined by a user and stored in the system in advance, or an interface by which the way of sorting can be selected by a user on a screen may be provided.

While the invention made by the inventors of the present invention has been concretely described based on the embodiments in the foregoing, it is needless to say that the present invention is not limited to the foregoing embodiments and various modifications and alterations can be made within the scope of the present invention.

INDUSTRIAL APPLICABILITY

The present invention relates to sample test automation system and can be widely applied particularly to a system, an apparatus, etc. which carries out conveyance by a sample holder on which only one sample is installed.

The invention claimed is:
1. A sample test automation system for subjecting samples to various processes, the sample test automation system comprising:
　　a sample introducing unit configured to hold a plurality of sample trays each having a same shape and each having a plurality of samples to be processed in the sample test automation system held in a plurality of sample containers placed on each of the sample trays, wherein the sample introducing unit has a sample transfer arm configured to transfer individual ones of the sample containers from the sample trays to a plurality of sample holders;

a conveying unit configured to convey the sample containers in the sample holders to destinations corresponding to the various processes; and an operation control unit that is programmed to control operation of the sample introducing unit and the conveying unit, wherein a plurality of tags including information for distinguishing individual ones of the sample trays from the other sample trays are attached to the sample trays, wherein the operation control unit is programmed to display a setting screen where process information, including one of a routine process and a priority process, is specified for each one of the sample trays in accordance with the information of the tags attached to the sample trays, wherein the sample introducing unit includes a plurality of tag readers and a plurality of tray storage units each having a same shape to hold one of the sample trays and having one of the tag readers disposed therein, and each of the tag readers is configured to read one of the tags attached to one of the sample trays when the one of the sample trays is placed on a corresponding one of the tray storage units, wherein the operation control unit is programmed to acquire the process information of the read tags when two or more sample trays are placed on the tray storage units, determine a priority sample tray from among the sample trays placed on the tray storage units, where the priority sample tray is determined to have the priority process based on the specified process information acquired from the read tags attached to the sample trays placed on the tray storage units, wherein the operation control unit is further programmed to control the sample transfer arm to transfer the one or more sample containers of the determined priority sample tray to the sample holders prior to transferring the one or more sample containers of the other sample trays placed on the tray storage units to the sample holders.

2. The sample test automation system according to claim 1, wherein each one of the sample trays is logically compartmentalized into a plurality of sections, and wherein, the operation control unit is further programmed to control the sample transfer arm to transfer the one or more sample containers from a first one of the sections of the priority sample tray to the sample holders prior to transferring the one or more sample containers from the other section of the priority sample tray to the sample holders.

3. The sample test automation system according to claim 1, wherein the tags further include information on at least one of: a type of the samples mounted thereon, necessity/non-necessity of a centrifugal separation process of the samples mounted thereon, necessity/non-necessity of a decapping process of the samples mounted thereon, necessity/non-necessity of a recapping process of the samples mounted thereon, information about a conveyance destination of the samples mounted thereon, a shape of containers holding the samples mounted thereon, and a type of the containers holding the samples mounted thereon.

4. The sample test automation system according to claim 3, further comprising:

a display coupled to the operation control unit, wherein the operation control unit is further programmed to display the setting screen on the display, and wherein the information about the sample trays and the information about the samples are specified before placing the sample trays on the tray storage units.

5. The sample test automation system according to claim 1, wherein the operation control unit is coupled to the sample transfer arm and the conveying unit, and wherein the operation control unit is programmed to control the conveying unit to convey the individual ones of the sample containers in the sample holders that were transferred from the determined priority sample tray to a destination corresponding to one of the various processes.

* * * * *